(12) United States Patent
Talanian et al.

(10) Patent No.: US 6,288,037 B1
(45) Date of Patent: *Sep. 11, 2001

(54) SUBSTRATES AND INHIBITORS FOR CYSTEINE PROTEASE ICH-1

(75) Inventors: Robert V. Talanian, Harvard; Tariq Ghayur, Grafton, both of MA (US); John C. Hodges, Ann Arbor, MI (US)

(73) Assignees: BASF Aktiengesellschaft, Ludwigshafen (DE); Warner-Lambert Company, Morris Plains, NJ (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/665,643

(22) Filed: Jun. 18, 1996

Related U.S. Application Data

(63) Continuation-in-part of application No. 08/592,943, filed on Jan. 29, 1996, now abandoned.

(51) Int. Cl.$^7$ .............................. A61K 38/07; C07K 5/10
(52) U.S. Cl. ........................... 514/17; 530/329; 530/330; 435/219
(58) Field of Search .............................. 514/17; 530/329, 530/330; 435/219

(56) References Cited

U.S. PATENT DOCUMENTS

| 5,416,013 | 5/1995 | Black et al. | 435/226 |
| 5,532,167 | * 7/1996 | Cantley et al. | 436/89 |

FOREIGN PATENT DOCUMENTS

| 0 519 748 A2 | 12/1992 | (EP) . |
| 0 547 699 A1 | 6/1993 | (EP) . |
| WO 91/15577 | 10/1991 | (WO) . |
| WO 93/05071 | 3/1993 | (WO) . |
| WO 93/14777 | 8/1993 | (WO) . |
| WO 93/16710 | 9/1993 | (WO) . |
| WO 94/00154 | 1/1994 | (WO) . |
| WO 95/00160 | 1/1995 | (WO) . |
| WO 96/00297 | 1/1996 | (WO) . |

OTHER PUBLICATIONS

Dayhoff et al., Atlas of Protein Sequence and Structure, vol. 5 pp. 89–99, 1972.*
Gilmer et al., J. Biol. Chem. vol. 269, No. 50 pp. 31711–31719, Dec. 1994.*
Nzcholson et al., Nature Biotech vol. 14 (Mar. 1996) pp. 297–301.*
Sleath et al., J. Biol. Chem. vol. 265 No. 24 Aug. 1990, pp. 14526–14528.*
Wang et al. J. Biol. Chem. vol. 270 No. 30 (Jul. 1995) pp. 18044–18050.*
Hind et al. J. Mot. Chem. vol. 34 (1991) pp. 1777–1789.*
Pinilla et al. Biochem. J. vol. 381 pp. 847–853. (1994).*
Fernandes–Alnemri, T., et al. "In Vitro Activation of CPP32 and Mch3 by Mch4, A Novel Human Apoptotic Cysteine Protease Containing Two FADD–Like Domains", *Proc. Natl. Acad. Sci.*, USA, vol. 93, pp. 7464–7469, 1996.
Dubrez, L., et al. "Pivotal Role of A DEVD–Sensitive Step In Etoposide–Induced And Fas–Mediated Apoptotic Pathways", *The EMBO Journal*, vol. 15, No. 20, pp. 5504–5512, 1996.
Fujita, E., et al. "Enhancement of CPP32–Like Activity In the TNF–Treated U937 Cells by the Proteasome Inhibitors", *Biochemical and Biophysical Research Communications*, vol. 224, pp. 74–79, 1996.
Nicholson, D. et al., "Identification and Inhibition of the ICE/CED–3 Protease Necessary For Mammalian Apoptosis", *Nature*, vol. 376, pp. 37–43, 1995.
Pinilla, C. et al., "Investigation of Antigen–Antibody Interactions Using A Soluble, Non–Support–Bound Synthetic Decapeptide Library Composed of Four Trillion ($4 \times 10^{12}$) Sequences", *Biochem. J.*vol. 301. pp. 847–853, 1996.
Wang, Xiaodong, et al., "Purification of an Interleukin–1β Converting Enzyme–Related Cysteine Protease That Cleaves Sterol Regulatory Element–Binding Proteins Between The Leucine Zipper and Transmembrane Domains", The Journal of Biological Chemistry, vol. 270, No. 30, pp. 18044–18050, 1995.
Munday, Neil A. et al., "Molecular Cloning and Pro–Apoptotic Activity of $ICE_{rel}II$ and $ICE_{rel}III$, Members of the ICE/CED–3 Family of Cysteine Proteases", *The Journal of Biological Chemistry*, vol. 270:26, pp. 15870–15876 (1995).
Ray, Caroline A. et al., "Viral Inhibition of Inflammation: Cowpox Virus Encodes an Inhibitor of the Interleukin–1β Converting Enzyme", *Cell*, vol. 9, pp. 597–604 (1992).
Reiter, Lawrence A. "Peptidic p–nitroanilide Substrates of Interleukin–1β–converting Enzyme", *Int. J. Peptide Protein Res.*, vol. 43, pp. 87–96 (1994).
Rich, Daniel H., "Inhibitors of Cysteine Proteinases", in *Protease Inhibitors*(Barrett and Salversen, eds.), *Elsevier Science Publishers*, pp. 153–178 (1986).
Tewari, Muneesh et al., "Yama/CPP32β, a Mammalian Homolog of CED–3, Is a CrmA–Inhibitable Protease That Cleaves the Death Substrate Poly (ADP–Ribose) Polymerase"*Cell*, vol. 81, pp. 801–809 (1995).

(List continued on next page.)

*Primary Examiner*—Bennett Celsa
(74) *Attorney, Agent, or Firm*—John Conway, Esq.; Lahive & Cockfield, LLP; Giulio A. DeConti, Jr.

(57) ABSTRACT

Substrates and inhibitors for the cysteine protease Ich-1 are disclosed. These compounds are designed based on an optimal minimal substrate for Ich-1 and include reversible inhibitors, irreversible inhibitors, selectively reversible inhibitors, chromogenic substrates, fluorogenic substrates and radiolabeled substrates/inhibitors. Pharmaceutical compositions comprising the compounds of the invention are also provided. Methods for inhibiting the proteolytic activity of Ich-1, methods for detecting the presence of Ich-1 and methods for isolating Ich-1 using the compounds of the invention are also disclosed.

21 Claims, No Drawings

OTHER PUBLICATIONS

Thornberry, Nancy A., "A Novel Heterodimeric Cysteine Protease is Required for Interleukin–1β Processing in Monocytes", *Nature*, vol. 356, pp. 768–774 (1992).

Thornberry, Nancy A., "Interleukin–1β Converting Enzyme", *Methods in Enzymology*, vol. 244, pp. 615–631 (1994).

Walker, N.P.C. et al., "Crystal Structure of the Cysteine Protease Interleukin–1β–Converting Enzyme: A (p20/–10)$_2$ Homodimer", *Cell*, vol. 78, pp. 343–352 (1994).

Wang, Lin et al., "Ich–1, an Ice/ced–3–Related Gene, Encodes Both Positive and Negative Regulators of Programmed Cell Death", *Cell*, vol. 78, pp. 739–750 (1994).

Wilson, Keith P., et al., "Structure and Mechanism of Interleukin–1β Converting Enzyme,"*Nature*, vol. 370, pp. 270–275 (1994).

Yuan, Junying, The C. Elegans Cell Death Gene ced–3 Encodes a Protein Similar to Mammalian Interleukin–1β–Converting Enzyme, *Cell*, vol. 75, pp. 641–652 (1993).

Black, Roy A. et al., "Generation of Biologically Active Interleukin–1β by Proteolytic Cleavage of the Inactive Precursor", *The Journal of Biological Chemistry*, vol. 263:19, pp. 9437–9442 (1988).

Cerretti, Douglas Pat et al., "Molecular Cloning of the Interleukin–1β Converting Enzyme", *Science*, vol. 256, pp. 97–100 (1992).

Faucheu, Chi et al., A Novel Human Protease Similar to the Interleukin–1β Converting Enzyme Induces Apoptosis in Transfected Cells, *The EMBO Journal*, vol. 14:9, pp. 1914–1922 (1995).

Fernandes–Alnemri, Teresa et al., CPP32, a Novel Human Apoptotic Protein with Homology to *Caenorhabditis Elegans* Cell Death Protein Ced–3 and Mammalian Interleukin–1β Converting Enzyme, *The Journal of Biological Chemistry*, vol. 269:49, pp. 30761–30764 (1994).

Fernandes–Alnemri, Teresa et al., Mch2, a New Member of the Apoptotic Ced–3/Ice Cysteine Protease Gene Family, *Cancer Research*, vol. 55, pp. 2737–2742 (1995).

Kamens, Joanne et al., Identification and Characterization of ICH–2, a Novel Member of the Interleukin–1β–converting Enzyme Family of Cysteine Proteases, *The Journal of Biological Chemistry*, vol. 270:25, pp. 15250–15256 (1995).

Kumar, Sharad et al., "Induction of Apoptosis by the Mouse Nedd2 Gene, Which Encodes a Protein Similar to the Product of the *Caenorhabditis Elegans* Cell Death Gene ced–3 and the Mammalian IL–1β–converting Enzymes", *Genes Dev.*, vol. 8, pp. 1613–1626 (1994).

Brocklehurst, Kieth et al., "Cysteine Proteases in Hydrolytic Enzymes", (A. Neuberger & K. Brocklehurst, eds.), *Elsevier Press*, pp. 98–111 (1987).

* cited by examiner

SEQUENCE LISTING

```
<160> NUMBER OF SEQ ID NOS:  89

<210> SEQ ID NO 1
<211> LENGTH: 12
<212> TYPE: PRT
<213> ORGANISM: Artificial Sequence
<220> FEATURE:
<223> OTHER INFORMATION: amino-terminal acetyl modification;
      carboxy-terminal amide modification
<223> OTHER INFORMATION: Description of Artificial Sequence: synthetic
      construct

<400> SEQUENCE: 1

Arg Gly Val Asp Gln Gln Asp Gly Lys Asn His Trp
  1               5                  10

<210> SEQ ID NO 2
<211> LENGTH: 14
<212> TYPE: PRT
<213> ORGANISM: Artificial Sequence
<220> FEATURE:
<223> OTHER INFORMATION: Description of Artificial Sequence: synthetic
      construct
<223> OTHER INFORMATION: amino-terminal acetyl modification;
      carboxy-terminal amide modification

<400> SEQUENCE: 2
```

Asn Glu Ala Tyr Val His Asp Ala Pro Val Arg Ser Leu Tyr
 1               5                  10

<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence: synthetic
      construct
<223> OTHER INFORMATION: amino-terminal acetyl modification;
      carboxy-terminal amide modification

<400> SEQUENCE: 3

Trp Gly Asp Glu Val Asp Gly Val Asp Glu Val Trp
 1               5                  10

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: synthetic
      construct
<223> OTHER INFORMATION: amino-terminal acetyl modification;
      carboxy-terminal amide modification

<400> SEQUENCE: 4

His Ser Leu Asp Asn Lys Asp Gly Pro Val Trp
 1               5                  10

<210> SEQ ID NO 5
<211> LENGTH: 12
<212> TYPE: PRT
<213> ORGANISM: Artificial Sequence
<220> FEATURE:
<223> OTHER INFORMATION: Description of Artificial Sequence: synthetic
      construct
<223> OTHER INFORMATION: amino-terminal acetyl modification;
      carboxy-terminal amide modification

<400> SEQUENCE: 5

Gly Glu Asp Met Gln Asp Asn Ser Gly Thr Tyr Trp
 1               5                  10

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: synthetic
      construct
<223> OTHER INFORMATION: amino-terminal acetyl modification;
      carboxy-terminal amide modification

<400> SEQUENCE: 6

Tyr Ser Asp Gln Met Asp Gly Phe His Asp Ser Trp
 1               5                  10

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: synthetic
      construct
<223> OTHER INFORMATION: amino-terminal acetyl modification;
      carboxy-terminal amide modification

```
<400> SEQUENCE: 7

Cys Gly Ile Glu Thr Asp Ser Gly Val Asp Trp
 1               5                  10

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: synthetic
      construct
<223> OTHER INFORMATION: amino-terminal acetyl modification;
      carboxy-terminal amide modification

<400> SEQUENCE: 8

Gly Val Asp Gln Gln Asp Gly Lys Asn Trp
 1               5                  10

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: synthetic
      construct
<223> OTHER INFORMATION: amino-terminal acetyl modification;
      carboxy-terminal amide modification

<400> SEQUENCE: 9

Val Asp Gln Gln Asp Gly Lys Asn Trp
 1               5

<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence: synthetic
      construct
<223> OTHER INFORMATION: amino-terminal acetyl modification;
      carboxy-terminal amide modification

<400> SEQUENCE: 10

Asp Gln Gln Asp Gly Lys Asn Trp
 1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: synthetic
      construct
<223> OTHER INFORMATION: amino-terminal acetyl modification;
      carboxy-terminal amide modification

<400> SEQUENCE: 11

Gln Gln Asp Gly Lys Asn Trp
 1               5

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence: synthetic
      construct
<223> OTHER INFORMATION: amino-terminal acetyl modification;
      carboxy-terminal amide modification
```

```
<400> SEQUENCE: 12

Val Asp Gln Gln Asp Gly Lys Trp
 1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: synthetic
      construct
<223> OTHER INFORMATION: amino-terminal acetyl modification;
      carboxy-terminal amide modification

<400> SEQUENCE: 13

Val Asp Gln Gln Asp Gly Trp
 1               5

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence: synthetic
      construct
<223> OTHER INFORMATION: amino-terminal acetyl modification;
      carboxy-terminal amide modification

<400> SEQUENCE: 14

Val Asp Gln Gln Asp Trp
 1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: synthetic
      construct
<223> OTHER INFORMATION: amino-terminal acetyl modification;
      carboxy-terminal amide modification

<400> SEQUENCE: 15

Ile Asp Gln Gln Asp Gly Trp
 1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: synthetic
      construct
<223> OTHER INFORMATION: amino-terminal acetyl modification;
      carboxy-terminal amide modification

<400> SEQUENCE: 16

Tyr Asp Gln Gln Asp Gly Trp
 1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: synthetic
      construct
<223> OTHER INFORMATION: amino-terminal acetyl modification;
``` carboxy-terminal amide modification

<400> SEQUENCE: 17

Leu Asp Gln Gln Asp Gly Trp
 1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: synthetic
      construct
<223> OTHER INFORMATION: amino-terminal acetyl modification;
      carboxy-terminal amide modification

<400> SEQUENCE: 18

Thr Asp Gln Gln Asp Gly Trp
 1               5

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: synthetic
      construct
<223> OTHER INFORMATION: amino-terminal acetyl modification;
      carboxy-terminal amide modification

<400> SEQUENCE: 19

Asn Asp Gln Gln Asp Gly Trp
 1               5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: synthetic
      construct
<223> OTHER INFORMATION: amino-terminal acetyl modification;
      carboxy-terminal amide modification

<400> SEQUENCE: 20

Ala Asp Gln Gln Asp Gly Trp
 1               5

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: synthetic
      construct
<223> OTHER INFORMATION: amino-terminal acetyl modification;
      carboxy-terminal amide modification

<400> SEQUENCE: 21

Asp Asp Gln Gln Asp Gly Trp
 1               5

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: synthetic
      construct

```
<223> OTHER INFORMATION: amino-terminal acetyl modification;
      carboxy-terminal amide modification

<400> SEQUENCE: 22

Val Ser Gln Gln Asp Gly Trp
 1               5

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: synthetic
      construct
<223> OTHER INFORMATION: amino-terminal acetyl modification;
      carboxy-terminal amide modification

<400> SEQUENCE: 23

Val Glu Gln Gln Asp Gly Trp
 1               5

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: synthetic
      construct
<223> OTHER INFORMATION: amino-terminal acetyl modification;
      carboxy-terminal amide modification

<400> SEQUENCE: 24

Val Ala Gln Gln Asp Gly Trp
 1               5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: synthetic
      construct
<223> OTHER INFORMATION: amino-terminal acetyl modification;
      carboxy-terminal amide modification

<400> SEQUENCE: 25

Val Asn Gln Gln Asp Gly Trp
 1               5

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: synthetic
      construct
<223> OTHER INFORMATION: amino-terminal acetyl modification;
      carboxy-terminal amide modification

<400> SEQUENCE: 26

Val Tyr Gln Gln Asp Gly Trp
 1               5

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: synthetic
```

```
            construct
<223> OTHER INFORMATION: amino-terminal acetyl modification;
      carboxy-terminal amide modification

<400> SEQUENCE: 27

Val Asp Val Gln Asp Gly Trp
 1               5

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: synthetic
      construct
<223> OTHER INFORMATION: amino-terminal acetyl modification;
      carboxy-terminal amide modification

<400> SEQUENCE: 28

Val Asp Glu Gln Asp Gly Trp
 1               5

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: synthetic
      construct
<223> OTHER INFORMATION: amino-terminal acetyl modification;
      carboxy-terminal amide modification

<400> SEQUENCE: 29

Val Asp Thr Gln Asp Gly Trp
 1               5

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: synthetic
      construct
<223> OTHER INFORMATION: amino-terminal acetyl modification;
      carboxy-terminal amide modification

<400> SEQUENCE: 30

Val Asp Leu Gln Asp Gly Trp
 1               5

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: synthetic
      construct
<223> OTHER INFORMATION: amino-terminal acetyl modification;
      carboxy-terminal amide modification

<400> SEQUENCE: 31

Val Asp Ala Gln Asp Gly Trp
 1               5

<210> SEQ ID NO 32
<211> LENGTH: 7
<212> TYPE: PRT
<213> ORGANISM: Artificial Sequence
<220> FEATURE:
```

```
<223> OTHER INFORMATION: Description of Artificial Sequence: synthetic
      construct
<223> OTHER INFORMATION: amino-terminal acetyl modification;
      carboxy-terminal amide modification

<400> SEQUENCE: 32

Val Asp Tyr Gly Asp Gly Trp
  1               5

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: synthetic
      construct
<223> OTHER INFORMATION: amino-terminal acetyl modification;
      carboxy-terminal amide modification

<400> SEQUENCE: 33

Val Asp Asn Gln Asp Gly Trp
  1               5

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: synthetic
      construct
<223> OTHER INFORMATION: amino-terminal acetyl modification;
      carboxy-terminal amide modification

<400> SEQUENCE: 34

Val Asp Gln Ala Asp Gly Trp
  1               5

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: synthetic
      construct
<223> OTHER INFORMATION: amino-terminal acetyl modification;
      carboxy-terminal amide modification

<400> SEQUENCE: 35

Val Asp Gln Ser Asp Gly Trp
  1               5

<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence: synthetic
      construct
<223> OTHER INFORMATION: amino-terminal acetyl modification;
      carboxy-terminal amide modification

<400> SEQUENCE: 36

Val Asp Gln Lys Asp Gly Trp
  1               5

<210> SEQ ID NO 37
<211> LENGTH: 7
<212> TYPE: PRT
<213> ORGANISM: Artificial Sequence
```

```
<220> FEATURE:
<223> OTHER INFORMATION: Description of Artificial Sequence: synthetic
      construct
<223> OTHER INFORMATION: amino-terminal acetyl modification;
      carboxy-terminal amide modification

<400> SEQUENCE: 37

Val Asp Gln Val Asp Gly Trp
  1               5

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: synthetic
      construct
<223> OTHER INFORMATION: amino-terminal acetyl modification;
      carboxy-terminal amide modification

<400> SEQUENCE: 38

Val Asp Gln Met Asp Gly Trp
  1               5

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: synthetic
      construct
<223> OTHER INFORMATION: amino-terminal acetyl modification;
      carboxy-terminal amide modification

<400> SEQUENCE: 39

Val Asp Gln Leu Asp Gly Trp
  1               5

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: synthetic
      construct
<223> OTHER INFORMATION: amino-terminal acetyl modification;
      carboxy-terminal amide modification

<400> SEQUENCE: 40

Val Asp Gln Tyr Asp Gly Trp
  1               5

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: synthetic
      construct
<223> OTHER INFORMATION: amino-terminal acetyl modification;
      carboxy-terminal amide modification

<400> SEQUENCE: 41

Val Asp Gln Glu Asp Gly Trp
  1               5

<210> SEQ ID NO 42
<211> LENGTH: 7
<212> TYPE: PRT
```

```
<213> ORGANISM: Artificial Sequence
<220> FEATURE:
<223> OTHER INFORMATION: Description of Artificial Sequence: synthetic
      construct
<223> OTHER INFORMATION: amino-terminal acetyl modification;
      carboxy-terminal amide modification

<400> SEQUENCE: 42

Val Asp Gln Gln Glu Gly Trp
  1               5

<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: synthetic
      construct
<223> OTHER INFORMATION: amino-terminal acetyl modification;
      carboxy-terminal amide modification

<400> SEQUENCE: 43

Val Asp Val Ala Asp Gly Trp
  1               5

<210> SEQ ID NO 44
<211> LENGTH: 4
<212> TYPE: PRT
<213> ORGANISM: Artificial Sequence
<220> FEATURE:
<223> OTHER INFORMATION: Description of Artificial Sequence: synthetic
      construct
<223> OTHER INFORMATION: amino-terminal acetyl modification;
      carboxy-terminal amide modification

<400> SEQUENCE: 44

Tyr Val Ala Asp
  1

<210> SEQ ID NO 45
<211> LENGTH: 5
<212> TYPE: PRT
<213> ORGANISM: Artificial Sequence
<220> FEATURE:
<223> OTHER INFORMATION: Description of Artificial Sequence: synthetic
      construct

<400> SEQUENCE: 45

Val Asp Val Ala Asp
  1               5

<210> SEQ ID NO 46
<211> LENGTH: 5
<212> TYPE: PRT
<213> ORGANISM: Artificial Sequence
<220> FEATURE:
<223> OTHER INFORMATION: Description of Artificial Sequence: synthetic
      construct
<223> OTHER INFORMATION: amino-terminal acetyl modification;
      carboxy-terminal [CHO] modification

<400> SEQUENCE: 46

Val Asp Val Ala Asp
  1               5

<210> SEQ ID NO 47
<211> LENGTH: 5
<212> TYPE: PRT
<213> ORGANISM: Artificial Sequence
```

```
<220> FEATURE:
<223> OTHER INFORMATION: Description of Artificial Sequence: synthetic
      construct
<223> OTHER INFORMATION: amino-terminal acetyl modification;
      carboxy-terminal [CN] modification

<400> SEQUENCE: 47

Val Asp Val Ala Asp
  1               5

<210> SEQ ID NO 48
<211> LENGTH: 5
<212> TYPE: PRT
<213> ORGANISM: Artificial Sequence
<220> FEATURE:
<223> OTHER INFORMATION: Description of Artificial Sequence: synthetic
      construct
<223> OTHER INFORMATION: amino-terminal acetyl modification;
      carboxy-terminal [CHO] modification

<400> SEQUENCE: 48

Val Asp Val Ala Glu
  1               5

<210> SEQ ID NO 49
<211> LENGTH: 5
<212> TYPE: PRT
<213> ORGANISM: Artificial Sequence
<220> FEATURE:
<223> OTHER INFORMATION: Description of Artificial Sequence: synthetic
      construct
<223> OTHER INFORMATION: amino-terminal acetyl modification;
      carboxy-terminal [CN] modification

<400> SEQUENCE: 49

Val Asp Val Ala Glu
  1               5

<210> SEQ ID NO 50
<211> LENGTH: 5
<212> TYPE: PRT
<213> ORGANISM: Artificial Sequence
<220> FEATURE:
<223> OTHER INFORMATION: Description of Artificial Sequence: synthetic
      construct
<223> OTHER INFORMATION: amino-terminal acetyl modification;
      carboxy-terminal [COCH2Cl] modification

<400> SEQUENCE: 50

Val Asp Val Ala Asp
  1               5

<210> SEQ ID NO 51
<211> LENGTH: 5
<212> TYPE: PRT
<213> ORGANISM: Artificial Sequence
<220> FEATURE:
<223> OTHER INFORMATION: Description of Artificial Sequence: synthetic
      construct
<223> OTHER INFORMATION: amino-terminal acetyl modification;
      carboxy-terminal [COCH2OCOAr] modification

<400> SEQUENCE: 51

Val Asp Val Ala Asp
  1               5

<210> SEQ ID NO 52
<211> LENGTH: 5
<212> TYPE: PRT
```

```
<213> ORGANISM: Artificial Sequence
<220> FEATURE:
<223> OTHER INFORMATION: Description of Artificial Sequence: synthetic
      construct
<223> OTHER INFORMATION: amino-terminal acetyl modification;
      carboxy-terminal [COCH2S(CH2)aAr] modification

<400> SEQUENCE: 52

Val Asp Val Ala Asp
 1               5

<210> SEQ ID NO 53
<211> LENGTH: 5
<212> TYPE: PRT
<213> ORGANISM: Artificial Sequence
<220> FEATURE:
<223> OTHER INFORMATION: Description of Artificial Sequence: synthetic
      construct
<223> OTHER INFORMATION: amino-terminal acetyl modification;
      carboxy-terminal [COCH2O(CH2)aAr] modification

<400> SEQUENCE: 53

Val Asp Val Ala Asp
 1               5

<210> SEQ ID NO 54
<211> LENGTH: 5
<212> TYPE: PRT
<213> ORGANISM: Artificial Sequence
<220> FEATURE:
<223> OTHER INFORMATION: Description of Artificial Sequence: synthetic
      construct
<223> OTHER INFORMATION: amino-terminal acetyl modification;
      carboxy-terminal [COCH2S(CH2)aHetAr] modification

<400> SEQUENCE: 54

Val Asp Val Ala Asp
 1               5

<210> SEQ ID NO 55
<211> LENGTH: 5
<212> TYPE: PRT
<213> ORGANISM: Artificial Sequence
<220> FEATURE:
<223> OTHER INFORMATION: Description of Artificial Sequence: synthetic
      construct
<223> OTHER INFORMATION: amino-terminal acetyl modification;
      carboxy-terminal [COCH2O(CH2)aHetAr] modification

<400> SEQUENCE: 55

Val Asp Val Ala Asp
 1               5

<210> SEQ ID NO 56
<211> LENGTH: 5
<212> TYPE: PRT
<213> ORGANISM: Artificial Sequence
<220> FEATURE:
<223> OTHER INFORMATION: Description of Artificial Sequence: synthetic
      construct
<223> OTHER INFORMATION: amino-terminal acetyl modification;
      carboxy-terminal [COCH2(CH2)bAr] modification

<400> SEQUENCE: 56

Val Asp Val Ala Asp
 1               5

<210> SEQ ID NO 57
<211> LENGTH: 5
```

```
<212> TYPE: PRT
<213> ORGANISM: Artificial Sequence
<220> FEATURE:
<223> OTHER INFORMATION: Description of Artificial Sequence: synthetic
      construct
<223> OTHER INFORMATION: amino-terminal acetyl modification;
      carboxy-terminal [CO(CH2)bHetAr] modification

<400> SEQUENCE: 57

Val Asp Val Ala Asp
 1               5

<210> SEQ ID NO 58
<211> LENGTH: 5
<212> TYPE: PRT
<213> ORGANISM: Artificial Sequence
<220> FEATURE:
<223> OTHER INFORMATION: Description of Artificial Sequence: synthetic
      construct
<223> OTHER INFORMATION: amino-terminal acetyl modification;
      carboxy-terminal [CH2-S-S-CH2-Ph] modification

<400> SEQUENCE: 58

Val Asp Val Ala Asp
 1               5

<210> SEQ ID NO 59
<211> LENGTH: 5
<212> TYPE: PRT
<213> ORGANISM: Artificial Sequence
<220> FEATURE:
<223> OTHER INFORMATION: Description of Artificial Sequence: synthetic
      construct
<223> OTHER INFORMATION: amino-terminal acetyl modification;
      carboxy-terminal [CH2-S-S-2-Py] modification

<400> SEQUENCE: 59

Val Asp Val Ala Asp
 1               5

<210> SEQ ID NO 60
<211> LENGTH: 5
<212> TYPE: PRT
<213> ORGANISM: Artificial Sequence
<220> FEATURE:
<223> OTHER INFORMATION: Description of Artificial Sequence: synthetic
      construct
<223> OTHER INFORMATION: amino-terminal acetyl modification;
      carboxy-terminal [CH2-S-S-CH2-CH2-CH3]
      modification

<400> SEQUENCE: 60

Val Asp Val Ala Asp
 1               5

<210> SEQ ID NO 61
<211> LENGTH: 5
<212> TYPE: PRT
<213> ORGANISM: Artificial Sequence
<220> FEATURE:
<223> OTHER INFORMATION: Description of Artificial Sequence: synthetic
      construct
<223> OTHER INFORMATION: amino-terminal acetyl modification;
      carboxy-terminal
      [CH2-S-S-CH2-Asp-Ala-Val-Asp-Val-Ac] modification

<400> SEQUENCE: 61

Val Asp Val Ala Asp
 1               5
```

```
<210> SEQ ID NO 62
<211> LENGTH: 5
<212> TYPE: PRT
<213> ORGANISM: Artificial Sequence
<220> FEATURE:
<223> OTHER INFORMATION: Description of Artificial Sequence: synthetic
      construct
<223> OTHER INFORMATION: amino-terminal Aha modification; carboxy-terminal
      [CH2-S-S-CH2-Ph] modification

<400> SEQUENCE: 62

Val Asp Val Ala Asp
  1               5

<210> SEQ ID NO 63
<211> LENGTH: 5
<212> TYPE: PRT
<213> ORGANISM: Artificial Sequence
<220> FEATURE:
<223> OTHER INFORMATION: Description of Artificial Sequence: synthetic
      construct
<223> OTHER INFORMATION: amino-terminal Aha modification; carboxy-terminal
      [CH2-S-S-2-Py] modification

<400> SEQUENCE: 63

Val Asp Val Ala Asp
  1               5

<210> SEQ ID NO 64
<211> LENGTH: 5
<212> TYPE: PRT
<213> ORGANISM: Artificial Sequence
<220> FEATURE:
<223> OTHER INFORMATION: Description of Artificial Sequence: synthetic
      construct
<223> OTHER INFORMATION: amino-terminal Aha modification; carboxy-terminal
      [CH2-S-S-CH2-CH2-CH3] modification

<400> SEQUENCE: 64

Val Asp Val Ala Asp
  1               5

<210> SEQ ID NO 65
<211> LENGTH: 5
<212> TYPE: PRT
<213> ORGANISM: Artificial Sequence
<220> FEATURE:
<223> OTHER INFORMATION: Description of Artificial Sequence: synthetic
      construct
<223> OTHER INFORMATION: amino-terminal Aha modification; carboxy-terminal
      [CH2-S-S-CH2-Asp-Ala-Val-Asp-Val-Aha] modification

<400> SEQUENCE: 65

Val Asp Val Ala Asp
  1               5

<210> SEQ ID NO 66
<211> LENGTH: 5
<212> TYPE: PRT
<213> ORGANISM: Artificial Sequence
<220> FEATURE:
<223> OTHER INFORMATION: Description of Artificial Sequence: synthetic
      construct
<223> OTHER INFORMATION: amino-terminal Biotinyl Aha modification;
      carboxy-terminal [CH2-S-S-CH2-Ph] modification

<400> SEQUENCE: 66

Val Asp Val Ala Asp
  1               5
```

```
<210> SEQ ID NO 67
<211> LENGTH: 5
<212> TYPE: PRT
<213> ORGANISM: Artificial Sequence
<220> FEATURE:
<223> OTHER INFORMATION: Description of Artificial Sequence: synthetic
      construct
<223> OTHER INFORMATION: amino-terminal Biotinyl Aha modification;
      carboxy-terminal [CH2-S-S-2-Py] modification

<400> SEQUENCE: 67

Val Asp Val Ala Asp
  1               5

<210> SEQ ID NO 68
<211> LENGTH: 5
<212> TYPE: PRT
<213> ORGANISM: Artificial Sequence
<220> FEATURE:
<223> OTHER INFORMATION: Description of Artificial Sequence: synthetic
      construct
<223> OTHER INFORMATION: amino-terminal Biotinyl Aha modification;
      carboxy-terminal [CH2-S-S-CH2-CH2-CH3]
      modification

<400> SEQUENCE: 68

Val Asp Val Ala Asp
  1               5

<210> SEQ ID NO 69
<211> LENGTH: 5
<212> TYPE: PRT
<213> ORGANISM: Artificial Sequence
<220> FEATURE:
<223> OTHER INFORMATION: Description of Artificial Sequence: synthetic
      construct
<223> OTHER INFORMATION: amino-terminal Biotinyl Aha modification;
      carboxy-terminal
      [CH2-S-S-CH2-Asp-Ala-Val-Asp-Val-Aha] modification

<400> SEQUENCE: 69

Val Asp Val Ala Asp
  1               5

<210> SEQ ID NO 70
<211> LENGTH: 5
<212> TYPE: PRT
<213> ORGANISM: Artificial Sequence
<220> FEATURE:
<223> OTHER INFORMATION: Description of Artificial Sequence: synthetic
      construct
<223> OTHER INFORMATION: amino-terminal acetyl modification;
      carboxy-terminal [CHO] modification

<400> SEQUENCE: 70

Val Asp Val Ala Asp
  1               5

<210> SEQ ID NO 71
<211> LENGTH: 5
<212> TYPE: PRT
<213> ORGANISM: Artificial Sequence
<220> FEATURE:
<223> OTHER INFORMATION: Description of Artificial Sequence: synthetic
      construct
<223> OTHER INFORMATION: amino-terminal acetyl modification;
      carboxy-terminal [AMC] modification

<400> SEQUENCE: 71
```

Val Asp Val Ala Asp
1               5

<210> SEQ ID NO 72
<211> LENGTH: 5
<212> TYPE: PRT
<213> ORGANISM: Artificial Sequence
<220> FEATURE:
<223> OTHER INFORMATION: Description of Artificial Sequence: synthetic
      construct
<223> OTHER INFORMATION: amino-terminal acetyl modification;
      carboxy-terminal [para-NA] modification

<400> SEQUENCE: 72

Val Asp Val Ala Asp
1               5

<210> SEQ ID NO 73
<211> LENGTH: 5
<212> TYPE: PRT
<213> ORGANISM: Artificial Sequence
<220> FEATURE:
<223> OTHER INFORMATION: Description of Artificial Sequence: synthetic
      construct
<223> OTHER INFORMATION: amino-terminal acetyl modification;
      carboxy-terminal [ortho-NA] modification

<400> SEQUENCE: 73

Val Asp Val Ala Asp
1               5

<210> SEQ ID NO 74
<211> LENGTH: 5
<212> TYPE: PRT
<213> ORGANISM: Artificial Sequence
<220> FEATURE:
<223> OTHER INFORMATION: Description of Artificial Sequence: synthetic
      construct
<223> OTHER INFORMATION: amino-terminal acetyl modification;
      carboxy-terminal [CONHCH3] modification

<400> SEQUENCE: 74

Val Asp Val Ala Asp
1               5

<210> SEQ ID NO 75
<211> LENGTH: 5
<212> TYPE: PRT
<213> ORGANISM: Artificial Sequence
<220> FEATURE:
<223> OTHER INFORMATION: Description of Artificial Sequence: synthetic
      construct
<223> OTHER INFORMATION: amino-terminal acetyl modification;
      carboxy-terminal (Q)m-[CONH2] modification

<400> SEQUENCE: 75

Val Asp Val Ala Asp
1               5

<210> SEQ ID NO 76
<211> LENGTH: 7
<212> TYPE: PRT
<213> ORGANISM: Artificial Sequence
<220> FEATURE:
<223> OTHER INFORMATION: Description of Artificial Sequence: synthetic
      construct
<223> OTHER INFORMATION: amino-terminal acetyl modification;
      carboxy-terminal [CONH2] modification

```
<400> SEQUENCE: 76

Val Asp Val Ala Asp Gly Trp
 1               5

<210> SEQ ID NO 77
<211> LENGTH: 6
<212> TYPE: PRT
<213> ORGANISM: Artificial Sequence
<220> FEATURE:
<223> OTHER INFORMATION: Description of Artificial Sequence: synthetic
      construct
<223> OTHER INFORMATION: amino-terminal acetyl modification;
      carboxy-terminal [AMC] modification

<400> SEQUENCE: 77

Val Asp Val Ala Asp Gly
 1               5

<210> SEQ ID NO 78
<211> LENGTH: 6
<212> TYPE: PRT
<213> ORGANISM: Artificial Sequence
<220> FEATURE:
<223> OTHER INFORMATION: Description of Artificial Sequence: synthetic
      construct
<223> OTHER INFORMATION: amino-terminal acetyl modification;
      carboxy-terminal (2-C(3H)H2-C(3H)H-CH2)Gly-[CONH2]
      modification

<400> SEQUENCE: 78

Val Asp Val Ala Asp Gly
 1               5

<210> SEQ ID NO 79
<211> LENGTH: 6
<212> TYPE: PRT
<213> ORGANISM: Artificial Sequence
<220> FEATURE:
<223> OTHER INFORMATION: Description of Artificial Sequence: synthetic
      construct
<223> OTHER INFORMATION: amino-terminal acetyl modification;
      carboxy-terminal (125I)Tyr-[CONH2] modification

<400> SEQUENCE: 79

Val Asp Val Ala Asp Gly
 1               5

<210> SEQ ID NO 80
<211> LENGTH: 6
<212> TYPE: PRT
<213> ORGANISM: Artificial Sequence
<220> FEATURE:
<223> OTHER INFORMATION: Description of Artificial Sequence: synthetic
      construct
<223> OTHER INFORMATION: amino-terminal acetyl modification;
      carboxy-terminal (di125I)Tyr-[CONH2] modification

<400> SEQUENCE: 80

Val Asp Val Ala Asp Gly
 1               5

<210> SEQ ID NO 81
<211> LENGTH: 6
<212> TYPE: PRT
<213> ORGANISM: Artificial Sequence
<220> FEATURE:
<223> OTHER INFORMATION: Description of Artificial Sequence: synthetic
      construct
<223> OTHER INFORMATION: amino-terminal acetyl modification;
```

```
        carboxy-terminal [CONHCH2(4-HO-3-125I-5-Me-Ph)]
        modification

<400> SEQUENCE: 81

Val Asp Val Ala Asp Gly
  1               5

<210> SEQ ID NO 82
<211> LENGTH: 6
<212> TYPE: PRT
<213> ORGANISM: Artificial Sequence
<220> FEATURE:
<223> OTHER INFORMATION: Description of Artificial Sequence: synthetic
        construct
<223> OTHER INFORMATION: amino-terminal acetyl modification;
        carboxy-terminal [CONH(CH2)2(4-HO-3-125I-Ph)]
        modification

<400> SEQUENCE: 82

Val Asp Val Ala Asp Gly
  1               5

<210> SEQ ID NO 83
<211> LENGTH: 6
<212> TYPE: PRT
<213> ORGANISM: Artificial Sequence
<220> FEATURE:
<223> OTHER INFORMATION: Description of Artificial Sequence: synthetic
        construct
<223> OTHER INFORMATION: amino-terminal acetyl modification;
        carboxy-terminal [CONH(CH2)2(4-HO-3,5-di125I-Ph)]
        modification

<400> SEQUENCE: 83

Val Asp Val Ala Asp Gly
  1               5

<210> SEQ ID NO 84
<211> LENGTH: 6
<212> TYPE: PRT
<213> ORGANISM: Artificial Sequence
<220> FEATURE:
<223> OTHER INFORMATION: Description of Artificial Sequence: synthetic
        construct
<223> OTHER INFORMATION: amino-terminal Biotinyl Aha modification;
        carboxy-terminal (2-C(3H)H2-C(3H)H-CH2)Gly-[CONH2]
        modification

<400> SEQUENCE: 84

Val Asp Val Ala Asp Gly
  1               5

<210> SEQ ID NO 85
<211> LENGTH: 6
<212> TYPE: PRT
<213> ORGANISM: Artificial Sequence
<220> FEATURE:
<223> OTHER INFORMATION: Description of Artificial Sequence: synthetic
        construct
<223> OTHER INFORMATION: amino-terminal Biotinyl Aha modification;
        carboxy-terminal (125I)Tyr-[CONH2] modification

<400> SEQUENCE: 85

Val Asp Val Ala Asp Gly
  1               5

<210> SEQ ID NO 86
<211> LENGTH: 6
<212> TYPE: PRT
```

```
<213> ORGANISM: Artificial Sequence
<220> FEATURE:
<223> OTHER INFORMATION: Description of Artificial Sequence: synthetic
      construct
<223> OTHER INFORMATION: amino-terminal Biotinyl Aha modification;
      carboxy-terminal (di125I)Tyr-[CONH2] modification

<400> SEQUENCE: 86

Val Asp Val Ala Asp Gly
 1               5

<210> SEQ ID NO 87
<211> LENGTH: 6
<212> TYPE: PRT
<213> ORGANISM: Artificial Sequence
<220> FEATURE:
<223> OTHER INFORMATION: Description of Artificial Sequence: synthetic
      construct
<223> OTHER INFORMATION: amino-terminal Biotinyl Aha modification;
      carboxy-terminal [CONHCH2(4-HO-3-125I-5-Me-Ph)]
      modification

<400> SEQUENCE: 87

Val Asp Val Ala Asp Gly
 1               5

<210> SEQ ID NO 88
<211> LENGTH: 6
<212> TYPE: PRT
<213> ORGANISM: Artificial Sequence
<220> FEATURE:
<223> OTHER INFORMATION: Description of Artificial Sequence: synthetic
      construct
<223> OTHER INFORMATION: amino-terminal Biotinyl Aha modification;
      carboxy-terminal [CONH(CH2)2(4-HO-3-125I-Ph)]
      modification

<400> SEQUENCE: 88

Val Asp Val Ala Asp Gly
 1               5

<210> SEQ ID NO 89
<211> LENGTH: 6
<212> TYPE: PRT
<213> ORGANISM: Artificial Sequence
<220> FEATURE:
<223> OTHER INFORMATION: Description of Artificial Sequence: synthetic
      construct
<223> OTHER INFORMATION: amino-terminal Biotinyl Aha modification;
      carboxy-terminal [CONH(CH2)2(4-HO-3,5-di125I-Ph)]
      modification

<400> SEQUENCE: 89

Val Asp Val Ala Asp Gly
 1               5
```

SUBSTRATES AND INHIBITORS FOR CYSTEINE PROTEASE ICH-1

RELATED APPLICATION

This application is a continuation-in-part of U.S. patent application Ser. No. 08/592,943, filed Jan. 29, 1996 abandoned, the entire contents of which are hereby incorporated by reference.

BACKGROUND OF THE INVENTION

Ich-1 is a human cysteine protease that is a member of a family of cysteine proteases including interleukin-1β converting enzyme (ICE), a protein essential for the maturational processing of interleukin-1β (see e.g., Black, R. A., et al. (1988) *J. Biol. Chem.* 263:9437–9442; Kostura, M. J., et al. (1989) *Proc. Natl. Acad. Sci. USA* 86:5227–5231; Thornberry, N. A., et al. (1992) *Nature* 356:768–774; Ceretti, D. P., et al. (1992) *Science* 256:97–100) and the *Caenorhabditis elegans* protein Ced-3, a protein required for apoptosis during the development of *C. elegans* (see e.g., Yuan, J., et al. (1993) *Cell* 75:641–652). Other members of this family include CPP32/Yama (Fernandes-Alnemri, T., et al. (1994) *J. Biol. Chem.* 269:30761–30764; Tewari, M., et al. (1995) *Cell* 81:801–809), SCA (Wang, X., et al. (1995) *J. Biol Chem.* 270:18044–18050), Ich-2/ICE$_{rel}$II/Tx (Kamens, J., et al. (1995) *J. Biol Chem.* 270:15250–15256; Munday, N. A., et al. (1995) *J. Biol. Chem.* 270:15870–15876; Faucheu, C., et al. (1995) *EMBO J.* 14:1914–1922), ICE$_{rel}$III/Ty (Munday, N. A., et al. (1995) *J. Biol. Chem.* 270:15870–15876; Faucheau, C., et al. (1996) *Eur. J. Biochem.* 236:297–313), Mch2 (Fernandes-Alnemri, T., et al. (1995) *Cancer Res.* 55:2737–2742) and Mch3/ICE-LAP3/CMH-1 (Fernandes-Alnemri, T., et al. (1995) *Cancer Res.* 55:6045–6052; Duan, H., et al. (1996) *J. Biol. Chem.* 271:1621–1625; Lippke, J. A., et al. (1996) *J. Biol. Chem.* 271:1825–1828). The cDNA for Ich-1 has been isolated and the predicted amino acid sequence of Ich-1 displays approximately 30% amino acid identity to ICE (Wang, L. et al. (1994) *Cell* 78:739–750). The mouse homolog of Ich-1, termed Nedd2, also has been identified and similarly exhibits approximately 30% amino acid identity to ICE (Kumar, S., et al. (1994) *Genes Dev.* 8:1613–1626).

Members of the ICE-related family of proteins are involved in cytokine maturation leading to inflammation and in apoptosis. In particular, Ich-1 has been implicated in apoptosis and neuronal development. For example, Ich-1 (and its murine homolog Nedd2) induces apoptosis when overexpressed in mammalian cells (Kumar (1994) supra; Wang (1994) supra). Additionally, the Nedd2 gene was identified based upon its developmentally down-regulated expression in the adult brain (Kumar, S. et al. (1992) *Biochem. Biophys. Res. Commun.* 185:1155–1161). During murine embryonic development, the Nedd2 gene is ]highly expressed in several tissues undergoing a high rate of apoptosis, including the central nervous system (Kumar (1994) supra).

In vitro studies have demonstrated that ICE cleaves prointerleukin-1β at Asp$_{116}$-Ala$_{117}$ to release the fully active 17 kDa form (Black (1988) supra; Kostura (1989) supra). ICE also cleaves prointerleukin-1β at Asp$_{27}$-Ala$_{28}$ to release a 28 kDa form. Cleavage at these sites is dependent upon the presence of aspartic acid in the P1 position (the position immediately amino-terminal to the cleavage site) (Kostura (1989) supra, Howard, A., et al. (1991) *J. Immunol.* 147:2964–2969; Griffin, P. R., et al. (1991) *Int. J. Mass. Spectrom. Ion. Phys.* 111:131–149). However, an aspartic acid in the P1 position is not sufficient for ICE specificity. For example, several other proteins containing Asp-X bonds, including prointerleukin-1α, are not cleaved by ICE (Howard (1991) supra). An optimal minimal substrate for ICE has been identified as containing the tetrapeptide Tyr-Val-Ala-Asp (SEQ ID NO: 44) (Thornberry (1992) supra).

SUMMARY OF THE INVENTION

This invention provides the amino acid sequence of an optimal minimal substrate for Ich-1, and Ich-1 inhibitors and substrates designed based upon the preferred amino acid sequence specificity of Ich-1. The invention provides compounds of Formula I,

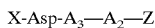

X-Asp-A$_3$—A$_2$—Z  I wherein:
 X is R$_1$—(W)$_n$—A$_5$, or R$_6$, wherein
  A$_5$ is a hydrophobic α-amino acid capable of interacting with the P5 site of Ich-1;
  W is any α-amino acid;
  n is an integer from 0–15;
  R$_1$ is hydrogen or an N-terminal acyl group selected from the group consisting of amides, carbamates, and ureas;
  R$_6$ is a hydrophobic N-terminal acyl group, selected from the group consisting of amides, carbamates and ureas, capable of interacting with the P5 site of Ich-1;
 Asp is an aspartic acid residue;
 A$_3$ is an α-amino acid capable of interacting with the P3 site of Ich-1;
 A$_2$ is an α-amino acid capable of interacting with the P2 site of Ich-1; and
 Z is A$_1$ or Asp-Y, wherein:
  A$_1$ is a residue that imparts Ich-1 inhibitory activity and is an aspartic acid or a glutamic acid residue that is modified at the C-terminus to contain an electrophilic center that is susceptible to nucleophilic attack or nucleophilic displacement by the sulfhydryl group of the active site cysteine residue of Ich-1; and
  Asp-Y is a pair of residues that impart Ich-1 substrate activity wherein Asp is an aspartic acid residue and Y is selected from the group consisting of a chromogenic leaving group, a fluorogenic leaving group, —(Q)$_m$—[CO$_2$H], and —(Q)$_m$-[CONHR$_2$], wherein Q is any α-amino acid or a radiolabeled derivative thereof, m is an integer from 1 to 15, and R$_2$ is selected from the group consisting of H, alkyl, alkenyl, cycloalkyl, (cycloalkyl)alkyl, aryl, arylalkyl, heterocycle, heteroaryl, heterocyclealkyl, heteroarylalkyl, and radiolabeled derivatives thereof.

The compounds of the invention can be incorporated into pharmaceutical compositions. Typically, the composition includes a compound of the invention and a pharmaceutically acceptable carrier.

The inhibitor compounds of the invention can be used, for example, to inhibit the proteolytic activity of Ich-1 by contacting Ich-1 with the inhibitor compound. The substrate compounds of the invention can be used, for example, to detect the presence of Ich-1 in a sample by contacting the sample with the substrate compound and detecting proteolytic cleavage of the substrate as an indicator of the presence of Ich-1 in the sample. In yet other embodiments, an inhibitor compound of the invention can be used to isolate Ich-1. For example, a biotinylated form of the inhibitor compound can be used in affinity purification of Ich-1.

DETAILED DESCRIPTION OF THE INVENTION

This invention provides inhibitor and substrate compounds for Ich-1, and methods of using these compounds, wherein the compounds are designed based upon an optimal minimal amino acid sequence for Ich-1 recognition. The Ich-1 sequence specificity is different from that of ICE, another cysteine protease to which Ich-1 is related. An initial peptide substrate for Ich-1 was identified using a series of peptides corresponding to known or suspected cleavage sites of ICE or ICE-related proteins, as described further in Example 1. This initial peptide was then modified by amino- and/or carboxy-terminal deletions and by amino acid substitutions, to define an optimal minimal substrate recognition site for Ich-1, as described further in Examples 2 and 3. A peptide containing the amino acid sequence Val-Asp-Val-Ala-Asp (VDVAD; SEQ ID NO: 45), corresponding to the P5, P4, P3, P2 and P1 positions, was thus defined as an optimal recognition sequence for Ich-1.

Amino acid substitutions within the optimal VDVAD-containing substrate demonstrated that maintenance of the P4 Asp and the P1 Asp was the most critical for maintenance of efficient cleavage of the substrate by Ich-1, whereas the P5, P3 and P2 positions were more amenable to substitutions (see Example 3). Accordingly, a consensus motif for Ich-1 recognition motif can be defined as $A_5$-Asp-$A_3$-$A_2$-Asp, wherein $A_5$, $A_3$ and $A_2$ are amino acids that are selected such that the site is recognized by Ich-1. Preferably, $A_5$ and $A_3$ are Val, and $A_2$ is Ala.

Definition of the amino acid sequence of the Ich-1 recognition site allows for the construction of substrates and inhibitors of Ich-1 designed based on this site. For example, peptide aldehyde inhibitors, such as acetyl-VDVAD-[CHO], can be prepared and used to inhibit the proteolytic activity of Ich-1, described further in Example 4. The acetyl-VDVAD-[CHO] inhibitor inhibits Ich-1 activity with an apparent $K_i$ value of 2.5 nM (see Example 4). Chromogenic or fluorogenic substrates, such as acetyl-VDVAD-7-amino-4-methylcoumarin, acetyl-VDVAD-para-nitroaniline and acetyl-VDVAD-ortho-nitroaniline, can also be prepared.

In order that the present invention may be more readily understood, certain terms are first defined.

As used herein, the term "P1 position" refers to the amino acid position immediately amino-terminal to the peptide bond cleaved by a protease (e.g., Ich-1), the term "P2 position" refers to the amino acid position immediately amino-terminal to the P1 position, the term "P3 position" refers to the amino acid position immediately amino-terminal to the P2 position, and so on. The term "P1' position" refers to the amino acid position immediately carboxy-terminal to the peptide bond cleaved by a protease, the term "P2' position" refers to the amino acid position immediately carboxy-terminal to the P1' position, and so on.

The term "Ich-1", as used herein, is intended to include proteins having the amino acid sequence of human Ich-1 as disclosed in Wang, L. et al., (1994) *Cell* 78:739–750, as well as modified forms thereof that retain the cysteine protease activity of naturally-occurring Ich-1. The term "Ich-1", as used herein, is also intended to include non-human homologs of human Ich-1, which may be known in the art by other names, such as Nedd2, the murine homolog of human Ich-1, the amino acid sequence of which is disclosed in Kumar, S. et al., (1994) *Genes Dev.* 8:1613–1626.

The term "inhibitor of Ich-1" (also referred to as an "Ich-1 inhibitor") refers to a compound that inhibits the cysteine protease activity of Ich-1. Depending on the particular compound used, inhibition may be partial or complete and may be reversible or irreversible.

The term "substrate for Ich-1" (also referred to as an "Ich-1 substrate") refers to a compound that is cleaved by Ich-1.

The term "alkyl", as used herein, refers to a straight or branched chain hydrocarbon group having from about 1 to 8 carbon atoms. The term "lower alkyl" refers to an alkyl group having from 1 to 6 carbon atoms (also referred to as $C_1$–$C_6$ alkyl). Exemplary lower alkyl groups include methyl, ethyl, n-propyl, isopropyl, n-butyl, isobutyl, sec-butyl, tert-butyl, n-pentyl, and n-hexyl. A $C_1$–$C_3$ alkyl refers to an alkyl group having 1 to 3 carbon atoms. An alkyl group may be unsubstituted, or may be substituted at one or more positions. If substituted, an alkyl preferably is substituted with one or two functional groups selected from —OH, —NH$_2$, —OCH$_3$, —CO$_2$H, —CO$_2$CH$_3$, —CONH$_2$, =O and —CN.

The terms "alkenyl" and "alkynyl", as used herein, refer to unsaturated groups analogous in length and possible substitution to the alkyls described above, but that contain at least one carbon-carbon double or triple bond respectively.

The term "cycloalkyl" refers to a cyclic saturated hydrocarbon group having from 3 to 8 carbon atoms. Exemplary cycloalkyls include cyclopropyl, cyclobutyl, cyclopentyl, cyclohexyl, and cyclooctyl. Cycloalkyl groups may be unsubstituted or substituted at one or more ring positions as described for alkyls. If substituted, cycloalkyl preferably is substituted with one or two functional groups selected from —OH, —NH$_2$, —OCH$_3$, —CO$_2$H, —CO$_2$CH$_3$, —CONH$_2$, =O and —CN.

The term "(cycloalkyl)alkyl" refers to a straight chain hydrocarbon from about one to five carbon atoms that is substituted by a cycloalkyl group as that group is defined above.

The term "aryl" as used herein includes 5-, 6- and 7-membered single-ring aromatic groups that are unsubstituted or may be substituted by one to four heteroatoms, such as benzene, pyrrole, furan, thiophene, imidazole, oxazole, thiazole, triazole, tetrazole, pyrazole, pyridine, pyrazine, pyridazine and pyrimidine, and the like. If substituted, the aromatic ring preferably is substituted by one to three functional groups selected from —CH$_3$, —CF$_3$, —F, —Cl, —Br, —I, —NO$_2$, —OH, —NH$_2$, —OCH$_3$, —CHO, —CH$_2$OH, —CO$_2$H, —CO$_2$CH$_3$, —CONH$_2$ and —CN. An aromatic ring may also be substituted with another aromatic ring, as in, for example, a biphenyl. Aryl groups also include fused or polycyclic aromatic systems such as naphthyl or quinolinyl.

The term "arylalkyl", as used herein, refers to a straight chain hydrocarbon from about one to five carbon atoms that is substituted by an aryl group as that group is defined above.

The term "heterocycle" refers to an aliphatic or aromatic five or six-membered ring, or an aromatic 5,6-fused or 6,6-fused bicyclic ring bearing one to four atoms selected from N, O and S. The rings can be unsubstituted or can be substituted by one to three functional groups selected from —CH$_3$, —CF$_3$, —F, —Cl, —Br, —I, —NO$_2$, —OH, —NH$_2$, —OCH$_3$, —CHO, —CH$_2$OH, —CO$_2$H, —CO$_2$CH$_3$, —CONH$_2$ and —CN.

The term "heteroaryl" refers to a subset of heterocycles, as defined above, the members of which contain at least one aromatic ring.

The term "(heterocycle)alkyl" refers to a straight chain hydrocarbon from about one to five carbon atoms that is substituted by a heterocycle group as that group is defined above.

The term "heteroarylalkyl" refers to a straight chain hydrocarbon from about one to five carbon atoms that is substituted by a heteroaryl group as that group is defined above.

The term "amino-terminal acyl group" refers to a chemical group attached to the amino group of an amino-terminal amino acid residue of a peptide of the present invention. Such acyl groups are well known and readily apparent to those skilled in the art, see e.g., Gross and Meienhofer (eds.), *The Peptides,* Academic Press, New York, pp. 3–81 (1981), U.S. Pat. Nos. 4,652,552 and 4,636,492. Examples of amino-terminal acyl groups include acetyl, biotinyl, biotinyl-6-amino-hexanoyl, $C_1$–$C_6$ alkyl carbonyl, $C_1$–$C_6$ alkoxycarbonyl (e.g., t-butoxycarbonyl (t-Boc)), benzoyl and benzyloxycarbonyl.

The term "carboxy-terminal modifying group having an electrophilic center that is susceptible to nucleophilic attack or nucleophilic displacement" refers to a chemical group susceptible to nucleophilic attack or displacement by the sulfhydryl group of the active site cysteine of Ich-1, thus modifying Ich-1 (reversibly or irreversibly) such that Ich-1 cannot interact with and cleave an Ich-1 substrate. Examples of such carboxy-terminal modifying groups include aldehydes, ketones and activated ketones, which have an electrophilic center susceptible to nucleophilic attack, and acyloxymethylketones, diazoalkylketones, haloalkylketones (e.g., fluoromethylketone, chloromethylketone) and thiol derivatives (e.g., disulfide-containing groups), which have an electrophilic center susceptible to nucleophilic displacement, leading to displacement of an electronegative leaving group.

An inhibitor compound of the invention, comprising a C-terminal modifying group, can inhibit the proteolytic activity of Ich-1 in either a "reversible" or "irreversible" manner, depending upon which C-terminal modifying group is utilized. For example, when the C-terminal group is subject to nucleophilic attack, such as a formyl group (i.e., a peptide aldehyde compound), inhibition of Ich-1 activity is reversible and the inhibitor compound is referred to as a reversible inhibitor. Alternatively, when the C-terminal modifying group is subject to nucleophilic displacement, such as a diazoalkylketone-containing compound, inhibition of Ich-1 activity is irreversible and the inhibitor compound is referred to as an irreversible inhibitor. As used herein, an "irreversible" inhibitor is one in which a covalent bond is formed between the enzyme and the inhibitor. Within the group of irreversible inhibitors, there also are certain inhibitors which are referred to as "selectively reversible", which means that inhibition is not spontaneously reversible (that is, the inhibition cannot be reversed simply by removal of the inhibitor from solution), but can be reversed by appropriate choice of conditions to yield the active enzyme. That is, when a covalent bond is formed between Ich-1 and a selectively reversible inhibitor, it is possible to cleave the covalent bond by appropriate choice of conditions, i.e., reagents, and restore enzyme activity. A preferred selectively reversible inhibitor compound of the invention comprises a disulfide moiety (i.e., the C-terminal modifying group is a thiol-derivative). Treatment of cysteine proteases (such as Ich-1) with disulfides results, via disulfide exchange, in a disulfide-containing cysteine protease (see e.g., D. Rich in "Proteinase Inhibitors", (1986), *Research Monographs in Cell and Tissue Physiology,* Vol. 12, A. J. Barrett and G. Salvesen, eds.). The active site sulfhydryl group of the enzyme is covalently modified and the enzyme is inactivated. However, treatment of the inactivated enzyme with a reagent that cleaves disulfide bonds (e.g., by reduction) results in recovery of enzyme activity. Exemplary reducing agents useful in cleaving disulfide bonds include dithiothreitol (DTT), 2-mercaptoethanol, glutathione, sodium borohydride, triphenylphosphine, zinc, and the like. A preferred reducing agent is DTT. The inhibition and restoration of enzyme activity can thereby conveniently be controlled.

The term "chromogenic leaving group" refers to a chemical group that, when cleaved from a compound of the invention, can absorb wavelengths within the visible range (i.e., approximately 400 to 750 mm) and thus appears colored. Preferred chromogenic leaving groups are para-nitroaniline (pNA) and ortho-nitroaniline (oNA).

The term "fluorogenic leaving group" refers to a chemical group that, when cleaved from a compound of the invention, can be measured fluorometrically. A preferred fluorogenic leaving group is 7-amino-4-methylcoumarin (AMC).

Standard three-letter and one-letter abbreviations for natural amino acids are used throughout this disclosure. Other common abbreviations, accepted in the art, that are used in this disclosure include: Aha (L-6-aminohexanoic acid), Cha (L-cyclohexylalanine), Abu (α-aminobutyric acid), Orn (ornithine), (2-Pr)Gly (L-propylglycine or L-2-aminopentanoic acid), (2-c-Pr)Gly (L-cyclopropylglycine or L-2-amino-2-cyclopropylacetic acid), (2-Et)Gly (L-ethylglycine or L-2-aminobutanoic acid), (2-t-Bu)Gly (L-t-butylglycine or L-2-amino-3,3-dimethylbutanoic acid), $^{125}I$ (iodine-125), $(2-C(^3H)H_2-C(^3H)H-CH_2)Gly$ (tritium-labeled L-propylglycine), Asp[CHO] (3-amino-3-formyl-propionic acid), Asp[CN] (3-amino-3-cyano-propionic acid), Glu[CHO] (4-amino-4-formyl-butanoic acid), Glu[CN] (4-amino-4-cyano-butanoic acid), Ar (an aryl group, as defined above), HetAr (a heteroaryl group, as defined above), biotin ((+)hexahydro-2-oxo-1H-thieno[3,4-d]imidazole-4-pentanoic acid), Ph (phenyl), Bz (benzyl), 2-Py (2-pyridyl) and Me (methyl).

The abbreviation Asp-CH$_2$—S— denotes the (S)-3-amino-4-thio-butanoic acid residue:

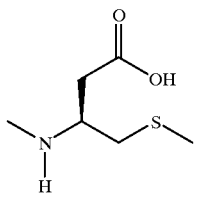

The term "ω-amino acid", as used herein, refers to a compound represented by the formula $H_2N-(CH_2)_m-CO_2H$, wherein m is 3–10. The skilled artisan will appreciate that the methylene units of the ω-amino acid may be substituted with the substituents of alkyl groups as described supra.

A derivative of the carboxy-terminus of a peptide is represented herein by the general formula —[CR], wherein C represents the carboxy terminus carbon and R represents a derivative group thereof. For example, —[COOH] represents a free carboxy terminus, —[CONH$_2$] represents a C-terminal amide and —[CHO] represents a C-terminal formyl group.

Various aspects of the invention are described in further detail in the following subsections.

I. Compounds of the Invention

The invention provides compounds of the general Formula I:

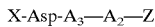

X-Asp-A$_3$—A$_2$—Z        I wherein:
X is $R_1$—$(W)_n$—$A_5$ or $R_6$, wherein
  $A_5$ is a hydrophobic α-amino acid capable of interacting with the P5 site of Ich-1;
  W is any α-amino acid;
  n is an integer from 0–15;
  $R_1$ is hydrogen or an N-terminal acyl group selected from the group consisting of amides, carbamates, and ureas;
  $R_6$ is a hydrophobic N-terminal acyl group, selected from the group consisting of amides, carbamates and ureas, capable of interacting with the P5 site of Ich-1;
Asp is an aspartic acid residue;
$A_3$ is an α-amino acid capable of interacting with the P3 site of Ich-1;
$A_2$ is an α-amino acid capable of interacting with the P2 site of Ich-1; and
Z is $A_1$ or Asp-Y, wherein:
  $A_1$ is a residue that imparts Ich-1 inhibitory activity and is an aspartic acid or a glutamic acid residue that is modified at the C-terminus to contain an electrophilic center that is susceptible to nucleophilic attack or nucleophilic displacement by the sulfhydryl group of the active site cysteine residue of Ich-1; and
  Asp-Y is a pair of residues that impart Ich-1 substrate activity wherein Asp is an aspartic acid residue and Y is selected from the group consisting of a chromogenic leaving group, a fluorogenic leaving group, —$(Q)_m$—$[CO_2H]$, and —$(Q)_m$—$[CONHR_2]$, wherein Q is any α-amino acid or a radiolabeled derivative thereof, m is an integer from 1 to 15, and $R_2$ is selected from the group consisting of H, alkyl, alkenyl, cycloalkyl, (cycloalkyl)alkyl, aryl, arylalkyl, heterocycle, heteroaryl, heterocyclealkyl, heteroarylalkyl, and radiolabeled derivatives thereof.
Preferably n is an integer from 0–10. More preferably n is an integer from 0–5.

In one embodiment, compounds of Formula I are compounds that inhibit the activity of Ich-1 (referred to herein as "Ich-1 inhibitor compounds" or simple "Ich-1 inhibitors"). An Ich-1 inhibitor is designed based upon the $A_5$-Asp-$A_3$—$A_2$-Asp consensus motif for Ich-1 recognition. For example, the Ich-1 inhibitor compound can comprise a peptide (or peptide derivative, peptide analog or peptide mimetic) based on the consensus motif, with a free N-terminal amino group (i.e., $R_1$ is hydrogen in the above formula) or, more preferably, modified by an amino-terminal acyl group (i.e., $R_1$ is an N-terminal acyl group in the above formula) and a C-terminal Asp or Glu residue that is modified with a modifying group having an electrophilic center susceptible to nucleophilic attack or nucleophilic displacement ($A_1$). The amino acid residues $A_5$, $A_3$ and $A_2$ within the motif (corresponding to the P5, P3 and P2 positions, respectively) are capable of interacting with the P5, P3 and P2 sites, respectively, of Ich-1. That is, these amino acid residues contribute to the binding of the compound to the P5, P3 and P2 sites, respectively, of Ich-1. Preferably, the $A_5$, $A_3$ and $A_2$ residues are selected such that the compound has Ich-1 inhibitor activity. Additional amino acids residues can be present amino-terminal to $A_5$ (($W)_n$). In certain embodiments, the $A_5$ position of the compound is substituted with a hydrophobic acyl group ($R_6$) that is capable of interacting with the P5 site of Ich-1.

In a preferred embodiment, the invention provides Ich-1 inhibitor compounds of the Formula I:

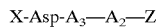

X-Asp-$A_3$—$A_2$—Z  I wherein:
X is $R_1$—$(W)_n$—$A_5$ or $R_6$, wherein
  $A_5$ is a hydrophobic α-amino acid capable of interacting with the P5 site of Ich-1;
  W is any α-amino acid;
  n is an integer from 0–15;
  $R_1$ is hydrogen or an N-terminal acyl group selected from the group consisting of amides, carbamates, and ureas;
  $R_6$ is a hydrophobic N-terminal acyl group, selected from the group consisting of amides, carbamates and ureas, capable of interacting with the P5 site of Ich-1;
Asp is an aspartic acid residue;
$A_3$ is an α-amino acid capable of interacting with the P3 site of Ich-1;
$A_2$ is an α-amino acid capable of interacting with the P2 site of Ich-1; and
Z is $A_1$ or Asp-Y, wherein:
  $A_1$ is a residue that imparts Ich-1 inhibitory activity and is an aspartic acid or a glutamic acid residue that is modified at the C-terminus to contain an electrophilic center that is susceptible to nucleophilic attack or nucleophilic displacement by the sulfhydryl group of the active site cysteine residue of Ich-1.

The amino-terminal acyl group, $R_1$, can be, for example, acetyl, biotinyl, biotinyl-6-amino-hexanoyl, $C_1$–$C_6$ alkyl carbonyl, $C_1$–$C_6$ alkoxycarbonyl, benzoyl and benzyloxycarbonyl. A preferred amino-terminal acyl group is an acetyl group. Preferably, n is 0–15, more preferably, n is 0–10 and even more preferably, n is 0–5. A preferred carboxy-terminal modifying group is —[CHO]. $A_5$, $A_3$, $A_2$ and $R_6$ can be selected using an in vitro proteolysis assay such as that described in Example 4. Briefly, to determine whether the compound has Ich-1 inhibitor activity, Ich-1 is incubated with both an Ich-1 substrate (e.g., Ac-VDVAD-AMC) and the compound and cleavage of the substrate is measured. A compound that decreases the amount of cleavage of the substrate (as compared to the amount of cleavage of the substrate in the absence of the compound) has "Ich-1 inhibitor activity", as that term is used herein.

In more preferred embodiments, the invention provides Ich-1 inhibitor compounds of Formula I:

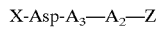

X-Asp-$A_3$—$A_2$—Z  I wherein:
X is $R_1$—$(W)_n$—$A_5$ or $R_6$, wherein
  $A_5$ is a hydrophobic α-amino acid selected from the group consisting of Val, Ile, Tyr, Phe, Leu, Thr, Asn, Cha, Abu, (2-n-Pr)Gly, (2-c-Pr)Gly, (2-t-Bu)Gly and (2-Et)Gly;
  W is any α-amino acid;
  n is an integer from 0 to 5;
  $R_1$ is hydrogen or $R_6$;
  $R_6$ is an N-terminal acyl group selected from the group consisting of Aha-, Biotinyl-, Biotinyl-Aha-, $R_3CO$—, $R_3CH_2CO$—, $R_3NHCO$—, $(R_4)_2NCO$—, and $R_3OCO$— wherein
    $R_3$ is selected from the group consisting of t-butyl, i-butyl, n-butyl, n-propyl, i-propyl, c-propyl, ethyl, methyl, c-hexyl, c-hexyl-$CH_2$—, c-hexyl-$(CH_2)_2$—, phenyl, phenyl-$CH_2$—, phenyl-$(CH_2)$ $_2$—, 4-hydroxyphenyl, 4-hydroxyphenyl-CH$_2$—, and 4-hydroxyphenyl-(CH$_2$)$_2$—; and R$_4$ is methyl or ethyl;

Asp is aspartic acid;

A$_3$ is an α-amino acid selected from the group consisting of Val, Glu, Thr, Ser, Gln, Ile, Abu, (2-n-Pr)Gly, (2-c-Pr)Gly, (2-t-Bu)Gly and (2-Et)Gly;

A$_2$ is an α-amino acid selected from the group consisting of Ala, Ser, Lys, Val, Met, Gln, Leu, Ile, Abu, His, Orn, Gly, (2-n-Pr)Gly, (2-c-Pr)Gly, (2-t-Bu)Gly and (2-Et)Gly; and Z is A$_1$, wherein:

A$_1$ is a C-terminally-modified residue selected from the group consisting of Asp[CHO], Asp[CN], Asp [COCHN$_2$], Asp[COCH$_2$Cl], Asp [COCH$_2$Br], Asp [COCH$_2$F], Asp[COCH$_2$OCO-Aryl], Asp [COCH$_2$OCO-Heteroaryl], Asp[COCH$_2$O(CH$_2$)$_a$-Aryl], Asp[COCH$_2$O(CH$_2$)$_a$-Heteroaryl], Asp [COCH$_2$S(CH$_2$)$_a$-Aryl], Asp[COCH$_2$S(CH$_2$)$_a$-Heteroaryl], Asp[CO(CH$_2$)$_b$-Aryl], Asp[CO(CH$_2$)$_b$-Heteroaryl], Asp[CH$_2$S-R$_5$], Glu[CHO], Glu[CN], Glu[COCHN$_2$], Glu[COCH$_2$Cl], Glu[COCH$_2$Br], Glu[COCH$_2$F], Glu[COCH$_2$OCO-Aryl], Glu [COCH$_2$OCO-Heteroaryl], Glu[COCH$_2$O(CH$_2$)$_a$-Aryl], Glu[COCH$_2$O(CH$_2$)$_a$-Heteroaryl], Glu [COCH$_2$S(CH$_2$)$_a$-Aryl], Glu[COCH$_2$S(CH$_2$)$_a$-Heteroaryl], Glu[CO(CH$_2$)$_b$-Aryl], Glu[CO(CH$_2$)$_b$-Heteroaryl], and Glu[CH$_2$SR$_5$] wherein a is an integer from 0 to 5;

b is an integer from 1 to 7; and

R$_5$ is selected from the group consisting of —S-alkyl, —S-cycloalkyl, —S-(cycloalkyl)alkyl, —S-aryl, —S-arylalkyl, —S-heterocycle, —S-(heterocycle)alkyl, —S-heteroaryl, —S-heteroarylalkyl, X-Asp-A$_3$—A$_2$—Asp (CH$_2$S)—, and X—Asp-A$_3$—A$_2$-Glu(CH$_2$S)—.

Preferably, A$_5$ is Val, A$_3$ is Val, A$_2$ is Ala and A$_1$ is Asp[CHO]. Thiol-derivative inhibitor compounds are selectively reversible inhibitor compounds that can form a disulfide bond with an active site sulfhydryl moiety of Ich-1 to inhibit Ich-1 activity. Subsequently, the disulfide bond can be cleaved with a reducing agent (e.g., DTT) to restore Ich-1 activity.

In even more preferred embodiments, the invention provides Ich-1 inhibitor compounds of Formula I:

$$X\text{-Asp-}A_3\text{—}A_2\text{—}Z \qquad \text{I}$$

wherein:

X is R$_1$—A$_5$, wherein

A$_5$ is Val;

R$_1$ is hydrogen or an N-terminal acyl group selected from the group consisting of CH$_3$CO—, PhCH$_2$OCO—, Aha-, Biotinyl-, and Biotinyl-Aha-;

A$_3$ is Val;

A$_2$ is Ala; and

Z is A$_1$, wherein

A$_1$ is a C-terminally-modified residue selected from the group consisting of Asp[CHO], Asp[CN], Asp [COCHN$_2$], Asp[COCH$_2$Cl], Asp[COCH$_2$Br], Asp [COCH$_2$—F], Asp[COCH$_2$OCO-Aryl], Asp [COCH$_2$OCO-Heteroaryl], Asp[COCH$_2$O(CH$_2$)$_a$-Aryl], Asp[COCH$_2$O(CH$_2$)$_a$-Heteroaryl], Asp [COCH$_2$S(CH$_2$)$_a$-Aryl], Asp[COCH$_2$S(CH$_2$)$_a$-Heteroaryl], Asp[CO(CH$_2$)$_b$-Aryl], Asp[CO(CH$_2$)$_b$-Heteroaryl], and Asp[CH$_2$S—R$_5$], wherein a is an integer from 0 to 5;

b is an integer from 1 to 7; and

R$_5$ is selected from the group consisting of —S-alkyl, —S-cycloalkyl, —S-(cycloalkyl)alkyl, —S-aryl, —S-arylalkyl, —S-heterocycle, —S-(heterocycle)alkyl, —S-heteroaryl, —S-heteroarylalkyl, and X-Asp-A$_3$—A$_2$—Asp (CH$_2$S)—.

In specific preferred embodiments, an Ich-1 inhibitor compound of the invention can comprise one of the following structures: Ac-Val-Asp-Val-Ala-Asp-[CHO], Ac-Val-Asp-Val-Ala-Asp-[CN], Ac-Val-Asp-Val-Ala-Glu-[CHO], Ac-Val-Asp-Val-Ala-Glu-[CN], Ac-Val-Asp-Val-Ala-Asp-[COCH$_2$Cl], Ac-Val-Asp-Val-Ala-Asp-[COCH$_2$OCOAr], Ac-Val-Asp-Val-Ala-Asp-[COCH$_2$S(CH$_2$)$_a$Ar], Ac-Val-Asp-Val-Ala-Asp-[COCH$_2$O(CH$_2$)$_a$Ar], Ac-Val-Asp-Val-Ala-Asp-[COCH$_2$S(CH$_2$)$_a$HetAr],Ac-Val-Asp-Val-Ala-Asp-[COCH$_2$O(CH$_2$)$_a$HetAr], Ac-Val-Asp-Val-Ala-Asp-[COCH$_2$(CH$_2$)$_b$Ar], Ac-Val-Asp-Val-Ala-Asp-[CO(CH$_2$)$_b$HetAr], Ac-Val-Asp-Val-Ala-Asp-[CH$_2$—S—S—CH$_2$—Ph], Ac-Val-Asp-Val-Ala-Asp-[CH$_2$—S—S-2-Py], Ac-Val-Asp-Val-Ala-Asp-[CH$_2$—S—S—CH$_2$—CH$_2$—CH$_3$], Ac-Val-Asp-Val-Ala-Asp-[CH$_2$——S—CH$_2$-Asp-Ala-Val-Asp-Ala-Val-Asp-Val-Ac],Aha-Val-Asp-Val-Ala-Asp [CH$_2$—S—S—CH$_2$—Ph], Aha-Val-Asp-Val-Ala-Asp-[CH$_2$—S—S-2-Py], Aha-Val-Asp-Val-Ala-Asp-[CH$_2$—S—S—CH$_2$—CH$_2$—CH$_3$] Aha-Val-Asp-Val-Ala-Asp-[CH$_2$—S—S—CH$_2$-Asp-Ala-Val-Asp-Val-Aha], Biotinyl-Aha-Val-Asp-Val-Ala-Asp-[CH$_2$—S—S—CH$_2$—Ph], Biotinyl-Aha-Val-Asp-Val-Ala-Asp-[CH$_2$—S—S-2-Py], Biotinyl-Aha-Val-Asp-Val-Ala-Asp-[CH$_2$—S—S—CH$_2$—CH$_2$—CH$_3$] and Biotinyl-Aha-Val-Asp-Val-Ala-Asp-[CH$_2$—S—S—CH$_2$-Asp-Ala-Val-Asp-Val-Aha], wherein a is an integer from 0 to 5 and b is an integer from 1 to 7.

The inhibitor compounds of the invention can be prepared using standard methods for peptide synthesis and peptide modification (e.g., at the amino and carboxy termini). Peptides can be synthesized by the Merrifield solid-phase technique, e.g., using an automated peptide synthesizer (e.g., Applied Biosystems 430A). For synthesis of peptides modified at the carboxy-terminus with a group having an electrophilic center susceptible to nucleophilic attack or displacement, see e.g., Chapman, (1992) *Bioorganic Medicinal Chemistry Letters* 2:613; PCT Publication No. WO 91/15577; Kettner, C. A., et al. (1974) *Arch. Biochem. Biophys.* 162:56; U.S. Pat. Nos. 4,582,821, 4,644,055; Kettner, C. A., et al. (1974) *Arch. Biochem. Biophys.* 165:739; Dakin, H. D. and West, R. (1928) *J. Biol. Chem.* 78:91; Rasnick, D., et al. (1985) *Anal. Biochem.* 149:461. Compounds having an aldehyde C-terminal modifying group preferably are synthesized by the method of Chapman. Compounds having a fluoromethyl ketone C-terminal modifying group preferably are synthesized by the method of Ranick. Compounds having a non-fluoro, haloalkyl ketone C-terminal modifying group preferably are synthesized by the method of Kettner. Compounds having a carboxy-terminal thiol derivative can be synthesized as described in U.S. patent application Ser. No. 08/573,896, entitled "Cysteine Protease Inhibitors and Uses Therefor, filed Dec. 18, 1995, the contents which are expressly incorporated herein by reference. Compounds can be purified by reverse phase HPLC and their structures confirmed by mass spectral analysis or NMR spectroscopy.

Alternatively, an inhibitor compound of the invention can be custom synthesized by a manufacturer that provides custom peptide synthesis (e.g., California Peptide Research, Inc., Napa Calif., or Bachem Bioscience, King of Prussia, Pa.).

Although the Ich-1 inhibitor compounds have been described hereinbefore with regard to the use of peptides and amino acids, it will be apparent to the skilled artisan that equivalent compounds can be constructed using peptide analogs, peptide derivatives and peptidomimetics and/or amino acid analogs, amino acid derivatives and amino acid mimetics. Any and all such compounds are intended to be encompassed by the present invention. As used herein, a "derivative" of a compound X (e.g., a peptide) refers to a form of X in which one or more reaction groups on the compound have been derivatized with a substituent group (e.g., alkylated or acylated peptides). As used herein an "analog" of a compound X refers to a compound that retains chemical structures of X necessary for functional activity of X yet that also contains certain chemical structures that differ from X. An example of an analog of a naturally-occurring peptide is a peptide that includes one or more non-naturally-occurring amino acids. As used herein, a "mimetic" of a compound X refers to a compound in which chemical structures of X necessary for functional activity of X have been replaced with other chemical structures that mimic the conformation of X. Examples of peptidomimetics include peptidic compounds in which the peptide backbone is substituted with one or more benzodiazepine molecules (see e.g., James, G. L. et al., (1993) *Science* 260:1937–1942) and "retro-inverso" peptides (see U.S. Pat. No. 4,522,752 by Sisto), described further below. A "residue" refers to an amino acid or amino acid mimetic incorporated in the peptide compound by an amide bond or amide bond mimetic. Approaches to designing peptide derivatives, analogs and mimetics are known in the art. For example, see Farmer, P. S. in *Drug Design* (E. J. Ariens, ed.) Academic Press, New York, 1980, vol. 10, pp. 119–143; Ball. J. B. and Alewood, P. F. (1990) *J. Mol. Recognition* 3:55; Morgan, B. A. and Gainor, J. A. (1989) *Ann. Rep. Med. Chem.* 24:243; and Freidinger, R. M. (1989) *Trends Pharmacol. Sci.* 10:270.

An "amino acid mimetic" refers to a moiety, other than a naturally occurring amino acid, that conformationally and functionally serves as a substitute for a particular amino acid in a peptide-containing compound without adversely interfering to a significant extent with the function of the compound (e.g., inactivation of Ich-1). In some circumstances, substitution with an amino acid mimetic may actually enhance properties of the inhibitor (e.g., interaction of the inhibitor with Ich-1). Examples of amino acid mimetics include D-amino acids. Peptides substituted with one or more D-amino acids may be made using well known peptide synthesis procedures. The effect of amino acid substitutions with D-amino acids and other peptidomimetics can be tested using assays as described infra.

The peptide analogs or mimetics of the invention include isosteres. The term "isostere" as used herein refers to a sequence of two or more residues that can be substituted for a second sequence because the steric conformation of the first sequence fits a binding site specific for the second sequence. The term specifically includes peptide backbone modifications (i.e., amide bond mimetics) well known to those skilled in the art. Such modifications include modifications of the amide nitrogen, the α-carbon, amide carbonyl, complete replacement of the amide bond, extensions, deletions or backbone crosslinks. Several peptide backbone modifications are known, including ψ[CH$_2$S], ψ[CH$_2$NH], ψ[C(S)NH$_2$], ψ[NHCO], ψ[C(O)CH$_2$], and ψ[(E) or (Z) CH=CH]. In the nomenclature used above, ψ indicates the absence of an amide bond. The structure that replaces the amide group is specified within the brackets. Other examples of isosteres include peptides substituted with one or more benzodiazepine molecules (see e.g., James, G. L. et al. (1993) *Science* 260:1937–1942).

Other possible modifications include an N-alkyl (or aryl) substitution (ψ[CONR]), backbone crosslinking to construct lactams and other cyclic structures, or retro-inverso amino acid incorporation (ψ[NHCO]). By "inverso" is meant replacing L-amino acids of a sequence with D-amino acids, and by "retro-inverso" or "enantio-retro" is meant reversing the sequence of the amino acids ("retro") and replacing the L-amino acids with D-amino acids. For example, if the parent peptide is Thr-Ala-Tyr, the retro modified form is Tyr-Ala-Thr, the inverso form is thr-ala-tyr, and the retro-inverso form is tyr-ala-thr (lower case letters refer to D-amino acids). Compared to the parent peptide, a retro-inverso peptide has a reversed backbone while retaining substantially the original spatial conformation of the side chains, resulting in a retro-inverso isomer with a topology that closely resembles the parent peptide and is able to bind the selected cysteine protease. See Goodman et al. *"Perspectives in Peptide Chemistry"* pp. 283–294 (1981). See also U.S. Pat. No. 4,522,752 by Sisto for further description of "retro-inverso" peptides.

In another embodiment, compounds of Formula I are compounds that have Ich-1 substrate activity (referred to herein as "Ich-1 substrate compounds" or simple "Ich-1 substrates"). An Ich-1 substrate is designed based upon the A$_5$-Asp-A$_3$—A$_2$-Asp consensus motif for Ich-1 recognition. For example, the Ich-1 substrate compound can comprise a peptide (or peptide analog, peptide derivative or peptidomimetic) based on the consensus motif, with a free amino-terminus (i.e., R$_1$ is hydrogen in the formulas below) or, more preferably, modified by an amino-terminal acyl group (i.e., R$_1$ is an N-terminal acyl group in the formulas below) and a free carboxy-terminus, or more preferably, a carboxy-terminal modifying group (Y) comprising a chromogenic leaving group, a fluorogenic leaving group, an α-amino acid amide (or derivative, analog or mimetic thereof) or a peptide amide (or derivative, analog or mimetic thereof). The amino acid residues A$_5$, A$_3$ and A$_2$ within the motif (corresponding to the P5, P3 and P2 positions, respectively) are capable of interacting with the P5, P3 and P2 sites, respectively, of Ich-1. That is, these amino acid residues contribute to the binding of the compound to the P5, P3 and P2 sites, respectively, of Ich-1. Preferably, the A$_5$, A$_3$ and A$_2$ residues are selected such that the compound has Ich-1 substrate activity. Additional amino acids residues can be present amino-terminal to A$_5$ ((W)$_n$). In certain embodiments, the A$_5$ position of the compound is substituted with a hydrophobic acyl group (R$_6$) that is capable of interacting with the P5 site of Ich-1. Additional amino acids residues also can be present carboxy-terminal to A$_1$ ((Q)$_m$).

In preferred embodiments, the invention provides Ich-1 substrate compounds of Formula I:

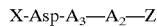

$$X\text{-Asp-}A_3\text{—}A_2\text{—}Z \qquad \qquad \text{I}$$

wherein:
X is R$_1$—(W)$_n$—A$_5$ or R$_6$, wherein
  A$_5$ is a hydrophobic α-amino acid capable of interacting with the P$_5$ site of Ich-1;
  W is any α-amino acid;
  n is an integer from 0–15;
  R$_1$ is hydrogen or an N-terminal acyl group selected from the group consisting of amides, carbamates, and ureas;
  R$_6$ is a hydrophobic N-terminal acyl group, selected from the group consisting of amides, carbamates, and ureas, capable of interacting with the P5 site of Ich-1;

Asp is an aspartic acid residue;

$A_3$ is an α-amino acid capable of interacting with the P3 site of Ich-1;

$A_2$ is an α-amino acid capable of interacting with the P2 site of Ich-1; and

Z is Asp-Y, wherein:

Asp-Y is a pair of residues that impart Ich-1 substrate activity wherein Asp is an aspartic acid residue and Y is selected from the group consisting of a chromogenic leaving group, a fluorogenic leaving group, —$(Q)_m$—$[CO_2H]$, and —$(Q)_m$—$[CONHR_2]$, wherein Q is any α-amino acid or a radiolabeled derivative thereof, m is an integer from 1 to 15, and $R_2$ is selected from the group consisting of H, alkyl, alkenyl, cycloalkyl, (cycloalkyl)alkyl, aryl, arylalkyl, heterocycle, heteroaryl, heterocyclealkyl, heteroarylalkyl, and radiolabeled derivatives thereof.

The amino-terminal acyl group ($R_1$) can be, for example, acetyl, biotinyl, biotinyl-6-amino-hexanoyl, $C_1$-$C_6$ alkyl carbonyl, $C_1$-$C_6$ alkoxycarbonyl, benzoyl and benzyloxycarbonyl. A preferred amino-terminal acyl group is an acetyl group. Preferably n is an integer from 0–10. More preferably, n is an integer from 0–5. Preferred carboxy-terminal modifying groups (Y) include the fluorogenic leaving group 7-amino-4-methylcoumarin and the chromogenic leaving groups para-nitroaniline and ortho-nitroaniline. Preferred radiolabeled derivatives of the carboxy-terminal modifying group are tritium and $^{125}I$ radiolabeled derivatives. $A_5$, $A_3$, $A_2$ and $R_6$ can be selected using an in vitro proteolysis assay, such as that described in the Examples. Briefly, to determine whether the compound has Ich-1 substrate activity, Ich-1 is incubated with the test compound and cleavage of the compound is measured. For example, when a pNA- or oNA-labeled compound is used, catalytic hydrolysis of the compound is monitored by the change in absorbance of the sample at 405 nm due to release of pNA or oNA as a function of time. Alternatively, when an AMC-labeled compound is used, cleavage of the compound is monitored using a spectrofluorimeter with an excitation wavelength of 380 nm and an emission wavelength of 460 nm. Alternatively, when the substrate has a free carboxy-terminus or is a peptide amide, cleavage of the compound can be analyzed, for example, by reverse phase HPLC using a 250×4.6 mm $C_{18}$ reverse phase column (Vydak, Hesperia, Calif.) and a linear gradient of MeCN—$H_2O$ with 0.1% (v/v) trifluoroacetic acid (TFA) (see Example 1). A compound that is cleaved by Ich-1 has "Ich-1 substrate activity", as that term is used herein.

In more preferred embodiments, the invention provides Ich-1 substrate compounds of Formula I:

$$X\text{-Asp-}A_3\text{—}A_2\text{—}Z \qquad \qquad I$$

wherein:

X is $R_1$—$(W)_n$—$A_5$ or $R_6$, wherein $A_5$ is a hydrophobic α-amino acid selected from the group consisting of Val, Ile, Tyr, Phe, Leu, Thr, Asn, Cha, Abu, (2-n-Pr)Gly, (2-c-Pr)Gly, (2-t-Bu)Gly and (2-Et)Gly;

W is any α-amino acid;

n is an integer of from 0 to 5;

$R_1$ is hydrogen or $R_6$;

$R_6$ is an N-terminal acyl group selected from the group consisting of Aha-, Biotinyl-, Biotinyl-Aha-, $R_3CO$—, $R_3CH_2CO$—, $R_3NHCO$—, $(R4)_2NCO$—, and $R_3OCO$— wherein $R_3$ is selected from the group consisting of t-butyl, i-butyl, n-butyl, n-propyl, i-propyl, c-propyl, ethyl, methyl, c-hexyl, c-hexyl-$CH_2$—, c-hexyl-$(CH_2)_2$—, phenyl, phenyl-$CH_2$—, phenyl-$(CH_2)_2$—, 4-hydroxyphenyl, 4-hydroxyphenyl-$CH_2$—, and 4-hydroxyphenyl-$(CH_2)_2$—; and $R_4$ is methyl or ethyl;

Asp is aspartic acid;

$A_3$ is an α-amino acid selected from the group consisting of Val, Glu, Thr, Ser, Gln, Ile, Abu, (2-n-Pr)Gly, (2-c-Pr)Gly, (2-t-Bu)Gly and (2-Et)Gly;

$A_2$ is an α-amino acid selected from the group consisting of Ala, Ser, Lys, Val, Met, Gln, Leu, Ile, Abu, His, Orn, Gly, (2-n-Pr)Gly, (2-c-Pr)Gly, (2-t-Bu)Gly and (2-Et)Gly; and Z is Asp-Y wherein Asp is aspartic acid; and Y is selected from the group consisting of 7 amino-4-methylcoumarin, para-nitroaniline, ortho-nitroaniline, and —$(Q)_m$—$[CONHR_2]$ wherein Q is selected from the group consisting of Ala, (2-allyl)Gly, (2-Pr)Gly, Gly, Tyr, and radiolabeled derivatives thereof;

m is 1 or 2;

$R_2$ is H, n-propyl, $CH_2CH_2$(4-hydroxyphenyl), $CH_2$(4-hydroxy-3-methylphenyl), and radiolabeled derivatives thereof.

Preferably, $A_5$ is Val, $A_3$ is Val and $A_2$ is Ala. Preferred radiolabeled derivatives are tritium and $^{125}I$ radiolabeled derivatives.

In even more preferred embodiments, the invention provides Ich-1 substrate compounds of Formula I:

$$X\text{-Asp-}A_3\text{—}A_2\text{—}Z \qquad \qquad I$$

wherein:

X is $R_1$—$A_5$, wherein $A_5$ is Val;

$R_1$ is selected from the group consisting of $CH_3CO$—, $PhCH_2OCO$—, Aha—, Biotinyl-, and Biotinyl-Aha-;

$A_3$ is Val;

$A_2$ is Ala; and

Z is Asp-Y wherein

Asp is aspartic acid; and

Y is selected from the group consisting of 7-amino-4-methylcoumarin, para-nitroaniline, ortho-nitroaniline, and —$(Q)_m$—$[CONHR_2]$ wherein Q is selected from the group consisting of Ala, (2-allyl)Gly, (2-Pr)Gly, Gly, Tyr, and radiolabeled derivatives thereof;

m is 1 or 2

$R_2$ is H, n-propyl, $CH_2CH_2$(4-hydroxyphenyl), $CH_2$(4-hydroxy-3-methylphenyl), and radiolabeled derivatives thereof.

Preferred radiolabeled derivatives are tritium and $^{125}I$ radiolabeled derivatives.

In specific preferred embodiments, an Ich-1 substrate compound of the invention can comprise one of the following structures: Ac-Val-Asp-Val-Ala-Asp-AMC, Ac-Val-Asp-Val-Ala-Asp-pNA, Ac-Val-Asp-Val-Ala-Asp-oNA, Ac-Val-Asp-Val-Ala-Asp-$[CONHCH_3]$, Ac-Val-Asp-Val-Ala-Asp-$(Q)_m$—$[CONH_2]$, Ac-Val-Asp-Val-Ala-Asp-Gly-Trp-$[CONH_2]$, Ac-Val-Asp-Val-Ala-Asp-Gly-AMC, Ac-Val-Asp-Val-Ala-Asp-Gly-(2-C($^3H$)$H_2$—C($^3H$)-H—$CH_2$)Gly-$[CONH_2]$, Ac-Val-Asp-Val-Ala-Asp-Gly-($^{125}I$)Tyr-$[CONH_2]$, Ac-Val-Asp-Val-Ala-Asp-Gly-(di$^{125}I$-)Tyr-$[CONH_2]$, Ac-Val-Asp-Val-Ala-Asp-Gly-$[CONHCH_2$(4-

HO-3-$^{125}$I-5-Me—Ph)], Ac-Val-Asp-Val-Ala-Asp-Gly-[CONH(CH$_2$)$_2$(4-HO-3-$^{125}$I-Ph)], Ac-Val-Asp-Val-Ala-Asp-Gly-[CONH(CH$_2$)$_2$(4-HO-3,5-di$^{125}$I-Ph)], Biotinyl-Aha-Val-Asp-Val-Ala-Asp-Gly-(2-C($^3$H)H$_2$—C($^3$H)H—CH$_2$)Gly-[CONH$_2$], Biotinyl-Aha-Val-Asp-Val-Ala-Asp-Gly-($^{125}$I)Tyr-[CONH$_2$], Biotinyl-Aha-Val-Asp-Val-Ala-Asp-Gly-(di$^{125}$I)Tyr-[CONH$_2$], Biotinyl-Aha-Val-Asp-Val-Ala-Asp-Gly-[CONHCH$_2$(4-HO-3-$^{125}$I-5-Me—Ph)], Biotinyl-Aha-Val-Asp-Val-Ala-Asp-Gly-[CONH(CH$_2$)$_2$(4-HO-$^{125}$-Ph)], and Biotinyl-Aha-Val-Asp-Val-Ala-Asp-Gly-[CONH(CH$_2$)$_2$(4-HO-3,5-di$^{125}$I-Ph)].

As described above for the inhibitor compounds, the substrate compounds of the invention can be prepared using standard methods for peptide synthesis and peptide modification (e.g., at the amino and carboxy termini). Peptides can be synthesized by the Merrifield solid-phase technique, e.g., using an automated peptide synthesizer (e.g., Applied Biosystems 430A). For synthesis of peptides modified at the carboxy-terminus with a 7-amino-4-methylcoumarin group, see e.g., Thornberry, N. A. et al. (1992) *Nature* 356:768–774 and PCT Publication WO 94/06906. For synthesis of peptides modified at the carboxy terminus with a paranitroaniline group, see e.g., Reiter, L. A. (1994) *Int. J. Peptide Protein Res.* 43:87–96. Compounds can be purified by reverse phase HPLC and their structures confirmed by mass spectral analysis or NMR spectroscopy.

Alternatively, a substrate compound of the invention can be custom synthesized by a manufacturer that provides custom peptide synthesis (e.g., California Peptide Research, Inc., Napa Calif., or Bachem Bioscience, King of Prussia, Pa.).

Although the Ich-1 substrate compounds have been described hereinbefore with regard to the use of peptides and amino acids, it will be apparent to the skilled artisan that equivalent compounds can be constructed using peptide analogs, peptide derivatives and peptidomimetics and/or amino acid analogs, amino acid derivatives and amino acid mimetics (as described further in the previous section with regard to the inhibitor compounds). Any and all such compounds are intended to be encompassed by the present invention.

II. Pharmaceutical Compositions

The compounds of the invention can be incorporated into pharmaceutical compositions suitable for administration to a subject. In a preferred embodiment, the pharmaceutical composition comprises either an inhibitor compound of the invention or a substrate compound of the invention and a pharmaceutically acceptable carrier.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous or parenteral administration (e.g., by injection). Depending on the route of administration, the active compound may be coated in a material to protect the compound from the action of acids and other natural conditions that may inactivate the compound.

A "pharmaceutically acceptable salt" refers to a salt that retains the desired biological activity of the parent compound and does not impart any undesired toxicological effects (see e.g., Berge, S. M., et al. (1977) *J. Pharm. Sci.* 66: 1–19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A compound of the present invention can be administered by a variety of methods known in the art. As will be appreciated by the skilled artisan, the route and/or mode of administration will vary depending upon the desired results. The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

The compounds can be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. The concentration of the compound in the compositions and preparations may, of course, be varied. The amount of compound in such therapeutically useful compositions is selected such that a suitable therapeutic dosage is obtained.

To administer a compound of the invention by other than parenteral administration, it may be necessary to coat the compound with, or co-administer the compound with, a material to prevent its inactivation. For example, the compound may be administered to a subject in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al., (1984) *J. Neuroimmunol.* 7:27). Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof.

Dosage regimens may be adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

IV. Uses of the Compounds of the Invention

The Ich-1 inhibitor compounds of the invention are useful for inhibiting the cysteine protease activity of Ich-1 (e.g., in an isolated preparation in vitro or within a cell, e.g., in culture or in a subject). The invention provides a method for inhibiting the proteolytic activity of Ich-1 comprising contacting Ich-1 with an inhibitor compound of the invention such that the proteolytic activity of Ich-1 is inhibited. To inhibit Ich-1 activity in a subject, the inhibitor compound is administered to the subject, as described further in the previous section. Depending upon which inhibitor compound is used, inhibition of Ich-1 activity can be reversible (e.g., with an aldehyde inhibitor) or irreversible (e.g., with a diazomethylketone inhibitor). Inhibition of Ich-1 activity in vitro is useful for characterizing Ich-1 and its involvement in the proteolysis of particular substrates. Moreover, an Ich-1 inhibitor compound of the invention can be used in the treatment of disease conditions where Ich-1 activity has a detrimental effect. Given the expression of Ich-1 in neuronal tissue, inhibition of Ich-1 activity may be useful in the treatment of neurodegenerative diseases, such as Alzheimer's disease, neuronal inflammation and stroke.

The Ich-1 substrate compounds of the invention are useful for detecting the presence of Ich-1, e.g., in an isolated preparation or within a cell. The invention provides a method for detecting the presence of Ich-1 in a sample comprising contacting a sample with a substrate compound of the invention and measuring the amount of proteolytic cleavage of the compound, wherein proteolytic cleavage of the compound is indicative of the presence of Ich-1 in the sample.

The reversible or selectively reversible inhibitor compounds of the invention also are useful for isolating Ich-1 from a mixture of substances, e.g., by affinity chromatography utilizing an affinity column comprising a reversible inhibitor compound. The invention provides a method for isolating Ich-1 from a mixture of substances comprising contacting a mixture of substances with a reversible or selectively reversible inhibitor compound of the invention (e.g., acetyl-VDVAD-[CHO] or acetyl-VDVAD-$CH_2$—S—S-Py), wherein the compound is immobilized (e.g., attached to a solid support), such that Ich-1 within the mixture of substances interacts with the compound, thereby forming immobilized Ich-1; separating immobilized Ich-1 from the mixture of substances; disrupting the interaction between immobilized Ich-1 and the compound; and recovering Ich-1 such that Ich-1 is isolated from the mixture of substances.

Preferably, the immobilized Ich-1 is separated from the remainder of the mixture of substances by washing the immobilized Ich-1 to remove the remainder of the mixture of substances. For reversible inhibitors, the interaction between the immobilized Ich-1 and the inhibitor compound can be disrupted, for example, by contacting the immobilized Ich-1 with excess free reversible inhibitor compound (e.g., if Ich-1 is immobilized on a column of Ac-VDVAD-[CHO] attached to a solid support, Ich-1 can be recovered by washing the column with excess free Ac-VDVAD-[CHO]). Alternatively, for selectively reversible inhibitors, wherein a covalent bond is formed between the inhibitor and the enzyme, the interaction between the immobilized Ich-1 and the inhibitor compound can be disrupted by contacting the immobilized Ich-1 with a reagent that cleaves the covalent bond between Ich-1 and the selectively reversible inhibitor. For example, a disulfide bond between the inhibitor compound and Ich-1 can be cleaved with a reducing agent, such as DTT or 2-mercaptoethanol.

In another embodiment, the invention provides a method of isolating Ich-1 from a mixture of substances comprising:

contacting a mixture of substances with a biotinylated Ich-1 inhibitor compound of the invention such that Ich-1 within the mixture of substances interacts with the biotinylated Ich-1 inhibitor compound, thereby forming biotinylated Ich-1;

immobilizing the biotinylated Ich-1 on an solid support, thereby forming immobilized, biotinylated Ich-1;

separating the immobilized, biotinylated Ich-1 from the mixture of substances;

disrupting the interaction between the immobilized, biotinylated Ich-1 and the biotinylated Ich-1 inhibitor compound; and recovering Ich-1, thereby isolating Ich-1.

In a preferred embodiment, the solid support is derivatized with streptavidin or avidin. Preferably, the separation step comprises washing the immobilized, biotinylated Ich-1 to remove the remainder of the mixture of substances. The interaction between the immobilized, biotinylated Ich-1 and the biotinylated Ich-1 inhibitor compound can be disrupted as described above (e.g., by contact with free reversible inhibitor or by contact with a reducing agent, such as DTT, when the inhibitor is a thiol derivative).

Solid supports suitable for use in the Ich-1 isolation methods of the invention are known in the art. (see, e.g., U.S. Pat. No. 5,380,656 to Barrett et al., and references cited therein), including, but not limited to, sepharose, modified to contain epoxide or N-hydroxysuccinimide ester groups, which are known to react with the amino function of ω-amino acids, and sepharose-avidin conjugate, which is known to bind biotinylated molecules. An inhibitor compound can be bound to a solid support in a variety of ways that are known in the art (see., e.g., G. A. Grant, ed. "Synthetic Peptides: A User's Guide" (1992), W. H. Freeman, Ch. 3, for methods of covalently linking a peptide to a solid support). An inhibitor compound can be bound to a solid support either covalently or non-covalently, by use of a suitable binding or linking moiety. In one embodiment, the linking moiety is attached by an amide bond to the inhibitor compound. The linking moiety may be, for example, an ω-amino acid, biotin or a combination thereof. In an exemplary embodiment, a carboxylate-substituted inhibitor compound (that comprises, for example, a carboxyl-substituted aryl moiety) can be covalently bound to an amino-derivatized solid support through formation of an amide bond, e.g., by condensation with dicyclohexylcarbodiimide, using standard methods. Methods of non-covalently binding compounds to an insoluble support are also well known. Exemplary non-covalent binding moieties include biotin (that binds to avidin or streptavidin), glutathione-S-transferase (that binds to glutathione) and polyhistidine (that binds to nickel ions, e.g., using a nickel column). A preferred binding moiety is biotin. An inhibitor compound can be substituted with a biotin moiety by attachment through, e.g., an amino group, such as a terminal amine or a side-chain amine. For additional description of the preparation and use of affinity columns for the purification of cysteine proteases, see e.g., PCT Publication No. WO 94/06906 and U.S. patent application Ser. No. 08/573,896, entitled "Cysteine Protease Inhibitors and Uses Therefor", filed Dec. 18, 1995, the contents of each of which are expressly incorporated herein by reference.

This invention is further illustrated by the following examples that should not be construed as limiting. The contents of all references, patents and published patent applications cited throughout this application are hereby incorporated by reference.

EXAMPLE 1
Identification of Peptide Substrates for Ich-1

To identify peptide substrates for Ich-1, candidate peptides were used in in vitro proteolysis assays with recombinant Ich-1 protein. Human Ich-1 enzyme (the nucleotide and amino acid sequences for which are disclosed in Wang, L., et al. (1994) *Cell* 78:739–750) was expressed recombinantly with an N-terminal polyhistidine tag by methods described in Kamens, J., et al. (1995) *J. Biol. Chem.* 270:15250–15256. The resulting enzyme, called N-His Ich-1, contains Ich-1 amino acid residues 167–435, with an initiator and polyhistidine tag fused to the amino terminus. The recombinant N-His Ich-1 protein was purified by metal chelating column chromatography as described in Porath, J. (1992) *Protein Expression and Purification* 3:263–281.

Candidate peptide substrates were synthesized by standard solid phase methods and were purified to ≧95% by reverse-phase chromatography. Peptide identities were confirmed by mass spectrometry. Each peptide was acetylated at the amino-terminus and amidated at the carboxy-terminus. The amino acid sequence of each peptide included at least one Trp or Tyr residue. Stock solutions of each peptide were prepared in dimethylsulfoxide (DMSO) at approximately 10 mM. The precise concentration of each stock solution was determined in duplicate as described in Edelhoch, H. (1967) *Biochemistry* 6:1948–1954. Dilutions of each stock solution to 500 μM were prepared and stored at −20° C. prior to use in enzyme assays.

To determine the substrate specificity of Ich-1, $V_{max}/K_m$ values for various candidate peptide substrates were compared using experimental procedures modeled after those of Howard, A., et al. (1991) *J. Immunol.* 147:2964–2969. Enzyme reaction mixtures (810 μL) were prepared containing: 100 mM sodium acetate (pH 6.2), 20% (v/v) glycerol, 5 mM dithiothreitol, 0.5 mM EDTA and approximately 15 μg N-His Ich-1. These mixtures were capped and preincubated for 30 minutes at 30° C. Candidate peptide substrates were added from 500 μM DMSO stocks to give final concentrations of 10 μM peptide and 2% (v/v) DMSO. The reaction mixtures were then capped and incubation was continued at 30° C. At 10 minute intervals for 60 minutes beginning at t=0, aliquots of 110 μL were removed from each reaction mixture and added to vials containing 11 μL of a solution of 3 M HCl in water to stop the enzyme reaction. Samples were stored at room temperature prior to analysis.

Samples were analyzed by reverse phase HPLC using a 250×4.6 mm $C_{18}$ reverse phase column (Vydak, Hesperia, Calif.) and a linear gradient of MeCN—$H_2O$ with 0.1% (v/v) TFA. The area under the substrate peaks (arbitrary units) was plotted vs. time of reaction for each substrate and fit into an equation of the form:

$$\frac{S_t}{S_0} = e^{-kt}$$

wherein $S_0$ is substrate peak area at time=0, $S_t$ is substrate peak area at time=t, e is a constant approximately equal to 2.718, k is the first order rate constant formally equal to $V_{max}/K_m$ and t is time. To obtain relative $V_{max}/K_m$ values, the results were normalized to a value of 1.00 for one peptide, typically that which displayed the highest $V_{max}/K_m$ value. Alternatively, results can be expressed as percent substrate cleavage after a fixed time of reaction.

In a first series of experiments, seven candidate peptides, corresponding to known or suspected cleavage sites for ICE or ICE-related proteins, were tested as Ich-1 substrates in the assay described above. The results are summarized below in Table 1 (wherein the aspartic acid residues at the P1 position in each peptide are aligned and indicated in bold).

TABLE 1

Cleavage by N-His Ich-1 of peptides that correspond to known or suspected ICE and ICE-related protein cleavage sites

| Peptide (SEQ ID NO.) | Sequence | % Cleavage after 60 minute reaction |
|---|---|---|
| 1 | acetyl-RGVDQQDGKNHW-amide | 80 |
| 2 | acetyl-NEAYVHDAPVRSLY-amide | 0 |
| 3 | acetyl-WGDEVDGVDEVW-amide | 0 |
| 4 | acetyl-HSLDNKDGPVW-amide | 0 |
| 5 | acetyl-GEDMQDNSGTYW-amide | 1 |
| 6 | acetyl-YSDQMDGFHDSW-amide | 0 |
| 7 | acetyl-CGIETDSGVDDW-amide | 8 |

One of the seven peptides (acetyl-RGVDQQDGKNHW-amide; Peptide 1; SEQ ID NO: 1), corresponding to amino acids 310–320 of human Ich-1 with an additional nonnaturally-occurring tryptophan residue (W) at the carboxy terminus, was cleaved at a rate significantly greater than the other tested peptides. The proteolytic cleavage products of Peptide 1 were purified by HPLC, and N-terminal sequencing by Edman degradation revealed that one of the two products contained the N-terminal sequence Gly-Lys-Asn. The other product gave no sequence, consistent with its identity as the N-terminal portion of Peptide 1, which is acetylated and therefore resistant to Edman degradation. Thus, it was concluded that the site of proteolytic cleavage is the second Asp in the peptide (i.e., the seventh amino acid residue from the amino-terminus).

EXAMPLE 2

Determination of the Length Dependence of Peptide Substrate Cleavage by Ich-1

In this example, to determine the length dependence of peptide cleavage by N-His Ich-1, a series of peptides based on Peptide 1 (SEQ ID NO: 1) but varying in length at the amino- and/or carboxy-termini were tested as substrates in proteolysis assays as described in Example 1. The results are summarized below in Table 2 (wherein the aspartic acid residues at the P1 position in each peptide are aligned and indicated in bold).

TABLE 2

Length dependence of peptide cleavage by N-His Ich-1

| Peptide (SEQ ID NO.) | Sequence | Relative ($V_{max}/K_m$) |
|---|---|---|
| Amino-terminal length variants | | |
| 1 | acetyl-RGVDQQDGKNHW-amide | [1.00] |
| 8 | acetyl-GVDQQDGKNW-amide | 0.65 |
| 9 | acetyl-VDQQDGKNW-amide | 0.74 |
| 10 | acetyl-DQQDGKNW-amide | 0.07 |
| 11 | acetyl-QQDGKNW-amide | 0.02 |
| Carboxy-terminal length variants | | |
| 9 | acetyl-VDQQDGKNW-amide | [1.00] |
| 12 | acetyl-VDQQDGKW-amide | 1.01 |
| 13 | acetyl-VDQQDGW-amide | 0.98 |
| 14 | acetyl-VDQQDW-amide | 0.93 |

The results shown in Table 2 using amino-terminal length variants demonstrate a strong dependence on the presence of a P5 residue for efficient cleavage by N-His Ich-1 (compare peptides 9 and 10). In contrast, peptides varying in their carboxy-terminal length (peptides 12, 13 and 14) are cleaved by N-His Ich-1 with similar ($V_{max}/K_m$) values, demonstrating that residues in those positions are relatively unimportant (compared to amino acids at P1 through P5) for recognition and cleavage by N-His Ich-1.

The requirement for a P5 residue for efficient cleavage by N-His Ich-1 is unexpected in view of similar experiments with ICE. ICE has been reported to require a P4 amino acid for efficient cleavage but cleavage by ICE is not enhanced further by the presence of a P5 residue (see Thornberry, N. A., et al. (1992) Nature 356:768–774). Thus, N-His Ich-1 differs from ICE in the former's requirement for a P5 residue for efficient cleavage.

EXAMPLE 3

Sequence Specificity of Peptide Substrate Cleavage by Ich-1

In this example, further experiments were performed to identify the particular amino acid preferences of N-His Ich-1 in positions P5, P4, P3, P2 and P1. A series of peptides based on Peptide 13 (SEQ ID NO: 13) but varying at the P5, P4, P3, P2 or P1 position were tested as substrates in proteolysis assays as described in Example 1. The results are summarized below in Table 3 (wherein the aspartic acid residues at the P1 position in each peptide are aligned and indicated in bold).

TABLE 3

Cleavage of peptide sequence variants by N-His Ich-1

| Peptide (SEQ ID NO.) | Sequence | Relative ($V_{max}/K_m$) |
|---|---|---|
| P5 position variants | | |
| 13 | acetyl-VDQQDGW-amide | [1.00] |
| 15 | acetyl-IDQQDGW-amide | 0.76 |
| 16 | acetyl-YDQQDGW-amide | 0.73 |
| 17 | acetyl-LDQQDGW-amide | 0.39 |
| 18 | acetyl-TDQQDGW-amide | 0.33 |
| 19 | acetyl-NDQQDGW-amide | 0.26 |
| 20 | acetyl-ADQQDGW-amide | 0.12 |
| 21 | acetyl-DDQQDGW-amide | 0.02 |
| P4 position variants | | |
| 13 | acetyl-VDQQDGW-amide | [1.00] |
| 22 | acetyl-VSQQDGW-amide | 0.18 |
| 23 | acetyl-VEQQDGW-amide | 0.03 |
| 24 | acetyl-VAQQDGW-amide | 0.01 |
| 25 | acetyl-VNQQDGW-amide | 0.00 |
| 26 | acetyl-VYQQDGW-amide | 0.00 |
| P3 position variants | | |
| 27 | acetyl-VDVQDGW-amide | 2.84 |
| 28 | acetyl-VDEQDGW-amide | 1.45 |
| 29 | acetyl-VDTQDGW-amide | 1.02 |
| 13 | acetyl-VDQQDGW-amide | [1.00] |
| 30 | acetyl-VDLQDGW-amide | 0.36 |
| 31 | acetyl-VDAQDGW-amide | 0.33 |
| 32 | acetyl-VDYQDGW-amide | 0.12 |
| 33 | acetyl-VDNQDGW-amide | 0.10 |
| P2 position variants | | |
| 34 | acetyl-VDQADGW-amide | 4.72 |
| 35 | acetyl-VDQSDGW-amide | 2.72 |
| 36 | acetyl-VDQKDGW-amide | 2.64 |
| 37 | acetyl-VDQVDGW-amide | 1.97 |
| 38 | acetyl-VDQMDGW-amide | 1.29 |
| 13 | acetyl-VDQQDGW-amide | [1.00] |
| 39 | acetyl-VDQLDGW-amide | 0.89 |
| 40 | acetyl-VDQYDGW-amide | 0.24 |
| 41 | acetyl-VDQEDGW-amide | 0.18 |
| P1 position variants | | |
| 13 | acetyl-VDQQDGW-amide | [1.00] |
| 42 | acetyl-VDQQEGW-amide | 0.17 |
| Predicted optimum variant | | |
| 43 | acetyl-VDVADGW-amide | 6.13 |
| 13 | acetyl-VDQQDGW-amide | [1.00] |

In the P5 position, N-His Ich-1 displays a preference for hydrophobic amino acids, with Val (Peptide 13) being most preferred. Polar amino acids (Thr and Asn; Peptides 18 and 19, respectively) are less preferred, and the weak cleavage of Peptide 21, containing Asp at P5, shows that charged amino acids at P5 are detrimental to cleavage by N-His Ich-1. Moreover, the strong preference of N-His Ich-1 for Val compared to Ala at P5 (compare Peptides 13 and 20) suggests that Val makes a positive contribution to cleavage by this enzyme.

In the P4 position, N-His Ich-1 displays a very strong preference for Asp (Peptide 13). Substitution with either Glu (Peptide 23; which maintains the expected negative charge at neutral pH of Asp) or Asn (Peptide 25; which is isosteric with Asp) is not tolerated. A positive contribution of P4 Asp to peptide cleavage is indicated by the relatively poor cleavage of Peptide 24, containing P4 Ala. Ser at P4 (Peptide 22) is tolerated, but is cleaved at a substantially lower efficiency than P4 Asp.

In the P3 position, a structurally wide range of amino acids is tolerated. Nevertheless, specific interaction of the P3 amino acid side chain with N-His Ich-1 is indicated by the strong preference observed for Val (Peptide 27) compared to Leu or Ala (Peptides 30 and 31, respectively).

In the P2 position, there is a preference for Ala (Peptide 34), but the structural diversity of other less preferred amino acids suggests that the P2 amino acid does not make a strong positive contribution to cleavage by N-His Ich-1. Nevertheless, peptides containing certain residues, such as Tyr or Glu (Peptides 40 and 41, respectively) are poorly cleaved compared to the most preferred peptides.

Regarding the P1 position, the modest cleavage of Peptide 42, containing P1 Glu, compared to Peptide 13, containing P1 Asp, demonstrates the specificity of N-His Ich-1 for Asp at P1 that is typical of ICE family proteases.

An optimal Ich-1 substrate was designed based on Peptide 13 containing substitutions of Val at P3 (as suggested by Peptide 27) and Ala at P2 (as suggested by Peptide 34). This optimal peptide substrate, Peptide 43, was preferred over Peptide 13 (relative $V_{max}/K_m$=6.13) to a greater extent than either of the single substituted peptides, Peptide 27 (relative $V_{max}/K_m$=2.84) or Peptide 34 (relative $V_{max}/K_m$=4.72). This result indicates that the positive contributions of P3 Val and P2 Ala are roughly additive when both are present, as in Peptide 43.

EXAMPLE 4
Inhibition of Ich-1 Proteolytic Activity

A peptidic aldehyde inhibitor of Ich-1 was designed based upon the optimal peptide substrate (Peptide 43) described in Example 3. An inhibitor having the structure acetyl-Val-Asp-Val-Ala-Asp-CHO (Ac-VDVAD-CHO) was synthesized by standard methods (e.g., as described in Chapman (1992) *Bioorganic Medicinal Chemistry Letters* 2:613). The ability of this peptidic aldehyde inhibitor to inhibit N-His Ich-1 activity was determined in in vitro proteolysis assays using a chromogenic para-nitroaniline-labeled peptide substrate. The peptide substrate had the structure acetyl-Val-Asp-Val-Ala-Asp-para-nitroaniline (AcYVAD-pNA) and was synthesized by standard methods (e.g., as described in Reiter, L. A. (1994) *Int. J Peptide Protein Res.* 43:87–96).

To perform the proteolysis assay, N-His Ich-1 was preincubated for 30 minutes at 30° C. in 160 μl of a reaction buffer containing 100 mM sodium acetate (pH 6.2), 20% (v/v) glycerol, 5 mM DTT, 0.5 mM EDTA, at pH 7.5. The peptide substrate was added in 40 μl of reaction buffer containing 2.0 mM substrate and 5% (v/v) DMSO solvent, giving final concentrations in the assay mixtures of 500 μM substrate and 1% (v/v) DMSO. The incubation of N-His Ich-1 with the peptide substrate at 30° C. was continued, and the catalytic hydrolysis of peptide substrate was monitored by the change in absorbance of the samples at 405 nm due to release of pNA as a function of time. Assays were performed in duplicate. Samples were read using a microtiter plate reader (Molecular Devices, Sunnyvale, Calif.). The Michaelis-Menten $K_m$ and $k_{cat}$ values for N-His Ich-1 were determined by standard methods. The results were as follows:

$K_m$: 42 μM $k_{cat}$: $0.12s^{-1}$

To examine the effect of the peptidic aldehyde inhibitor, enzyme samples were assayed as described above except that Ac-VDVAD-CHO was included in the reaction mixtures (11 separate reactions) at concentrations ranging from 0.1 nM to 10 μM. The results were fit to a sigmoidal curve, which yielded an $IC_{50}$ value of 8.0 nM. $IC_{50}$ values overstate apparent $K_i$ values by a factor of ($IC_{50}/(1+[S]/K_m)$), where [S] is the substrate concentration. Accordingly, from this an apparent $K_i$ value of 2.5 nM was calculated.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. An Ich-1 inhibitor compound of Formula I:

$$X\text{-Asp-}A_3\text{—}A_2\text{—}Z \quad\quad I$$

wherein:

X is $R_1$—(W)$_n$—$A_5$, wherein
 $A_5$ is Val;
 W is any α-amino acid;
 n is an integer from 0 to 5;
 $R_1$ is hydrogen or $R_6$;
 $R_6$ is an N-terminal acyl group selected from the group consisting of Aha-, Biotinyl-, Biotinyl-Aha-, $R_3$CO—, $R_3CH_2$CO—, $R_3$NHCO—, $(R_4)_2$NCO—, and $R_3$OCO— wherein
 $R_3$ is selected from the group consisting of t-butyl, i-butyl, n-butyl, n-propyl, i-propyl, c-propyl, ethyl, methyl, c-hexyl, c-hexyl-CH$_2$—, c-hexyl-(CH$_2$)$_2$—, phenyl, phenyl-CH$_2$—, phenyl-(CH$_2$)$_2$—, 4-hydroxyphenyl, 4-hydroxyphenyl-CH$_2$—, and 4-hydroxyphenyl(CH$_2$)$_2$—; and
 $R_4$ is methyl or ethyl;

Asp is aspartic acid;
$A_3$ is an α-amino acid selected from the group consisting of Val, Glu, Thr, Ser, Gln, Ile, Abu, (2-n-Pr)Gly, (2-c-Pr)Gly, (2-t-Bu)Gly and (2-Et)Gly;

$A_2$ is an α-amino acid selected from the group consisting of Ala, Ser, Lys, Val, Met, Gln, Leu, Ile, Abu, His, Orn, Gly, (2-n-Pr)Gly, (2-c-Pr)Gly, (2-t-Bu)Gly and (2-Et)Gly; and Z is $A_1$, wherein:
$A_1$ is a C-terminally-modified residue selected from the group consisting of Asp[CHO], Asp[CN], Asp[COCHN$_2$], Asp [COCH$_2$Cl], Asp[COCH$_2$Br], Asp[COCH$_2$F], Asp[COCH$_2$OCO-Aryl], Asp[COCH$_2$OCO-Heteroaryl], Asp[COCH$_2$O(CH$_2$)$_a$-Aryl], Asp[COCH$_2$O(CH$_2$)$_a$-Heteroaryl], Asp[COCH$_2$S(CH$_2$)$_a$-Aryl], Asp[COCH$_2$S(CH$_2$)$_a$-Heteroaryl], Asp[CO(CH$_2$)$_b$-Aryl], Asp[CO(CH$_2$)$_b$-Heteroaryl], Asp[CH$_2$S—R$_5$], Glu[CHO], Glu[CN], Glu[COCHN$_2$], Glu[COCH$_2$Cl], Glu[COCH$_2$Br], Glu[COCH$_2$F], Glu[COCH$_2$OCO-Aryl], Glu[COCH$_2$OCO-Heteroaryl], Glu[COCH$_2$O(CH$_2$)$_a$-Aryl], Glu[COCH$_2$O(CH$_2$)$_a$-Heteroaryl], Glu[COCH$_2$S(CH$_2$)$_a$-Aryl], Glu[COCH$_2$S(CH$_2$)$_a$-Heteroaryl], Glu[CO(CH$_2$)$_b$-Aryl], Glu[CO(CH$_2$)$_b$-Heteroaryl], and Glu[CH$_2$SR$_5$] wherein
a is an integer from 0 to 5;
b is an integer from 1 to 7; and
$R_5$ is selected from the group consisting of —S-alkyl, —S-cycloalkyl, —S-(cycloalkyl)alkyl, —S-aryl, —S-arylalkyl, —S-heterocycle, —S-(heterocycle)alkyl, —S-heteroaryl, —S-heteroarylalkyl, X-Asp-$A_3$—$A_2$-Asp(CH$_2$S)—, and X-Asp-$A_3$—$A_2$-Glu(CH$_2$S)—.

2. The compound of claim 1, wherein $A_3$ is Val.
3. The compound of claim 1, wherein $A_2$ is Ala.
4. The compound of claim 1, wherein $A_1$ is Asp[CHO].
5. An Ich-1 inhibitor compound of Formula I:

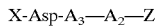

X-Asp-$A_3$—$A_2$—Z     I wherein:
X is $R_1$—$A_5$, wherein
$A_5$ is Val;
$R_1$ is selected from the group consisting of CH$_3$CO—, PhCH$_2$OCO—, Aha-, Biotinyl-, and Biotinyl-Aha-;
$A_3$ is Val;
$A_2$ is Ala; and
Z is $A_1$, wherein
$A_1$ is a C-terminally-modified residue selected from the group consisting of Asp[CHO], Asp[CN], Asp[COCHN$_2$], Asp[COCH$_2$Cl], Asp[COCH$_2$Br], Asp[COCH$_2$—F], Asp[COCH$_2$OCO-Aryl], Asp[COCH$_2$OCO-Heteroaryl], Asp[COCH$_2$O(CH$_2$)$_a$-Aryl], Asp[COCH$_2$O(CH$_2$)$_a$-Heteroaryl], Asp[COCH$_2$S(CH$_2$)$_a$-Aryl], Asp[COCH$_2$S(CH$_2$)$_a$-Heteroaryl], Asp[CO(CH$_2$)$_b$-Aryl], Asp[CO(CH$_2$)$_b$-Heteroaryl], and Asp[CH$_2$S—R$_5$], wherein
a is an integer from 0 to 5;
b is an integer from 1 to 7; and
$R_5$ is selected from the group consisting of —S-alkyl, —S-cycloalkyl, —S-(cycloalkyl)alkyl, —S-aryl, —S-arylalkyl, —S-heterocycle, —S-(heterocycle)alkyl, —S-heteroaryl, —S-heteroarylalkyl, and X-Asp-$A_3$—$A_2$-Asp(CH$_2$S)—.

6. An Ich-1 inhibitor compound selected from the group consisting of Ac-Val-Asp-Val-Ala-Asp-[CHO] (SEQ ID NO. 46), Ac-Val-Asp-Val-Ala-Asp-[CN] (SEQ ID NO. 47), Ac-Val-Asp-Val-Ala-Glu-[CHO] (SEQ ID NO. 48), Ac-Val-Asp-Val-Ala-Glu-[CN] (SEQ ID NO. 49), Ac-Val-Asp-Val-Ala-Asp-[COCH$_2$Cl] (SEQ ID NO. 50), Ac-Val-Asp-Val-Ala-Asp-[COCH$_2$OCOAr] (SEQ ID NO. 51), Ac-Val-Asp-Val-Ala-Asp-[COCH$_2$S(CH$_2$)$_a$Ar] (SEQ ID NO. 52), Ac-Val-Asp-Val-Ala-Asp-[COCH$_2$O(CH$_2$)$_a$Ar] (SEQ ID NO. 53), Ac-Val-Asp-Val-Ala-Asp-[COCH$_2$S(CH$_2$)$_a$HetAr] (SEQ ID NO. 54), Ac-Val-Asp-Val-Ala-Asp-[COCH$_2$O(CH$_2$)$_a$HetAr] (SEQ ID NO. 55), Ac-Val-Asp-Val-Ala-Asp-[COCH$_2$(CH$_2$)$_b$Ar] (SEQ ID NO. 56), Ac-Val-Asp-Val-Ala-Asp-[CO(CH$_2$)$_b$HetAr] (SEQ ID NO. 57), Ac-Val-Asp-Val-Ala-Asp-[CH$_2$—S—S—CH$_2$—Ph] (SEQ ID NO. 58), Ac-Val-Asp-Val-Ala-Asp-[CH$_2$—S—S-2-Py] (SEQ ID NO. 59), Ac-Val-Asp-Val-Ala-Asp-[CH$_2$—S—S—CH$_2$—CH$_2$—CH$_3$] (SEQ ID NO. 60), Ac-Val-Asp-Val-Ala-Asp-[CH$_2$—S—S—CH$_2$-Asp-Ala-Val-Asp-Val-Ac] (SEQ ID NO. 61), Aha-Val-Asp-Val-Ala-Asp-[CH$_2$—S—S—CH$_2$—Ph] (SEQ ID NO. 62), Aha-Val-Asp-Val-Ala-Asp-[CH$_2$—S—S-2-Py] (SEQ ID NO. 63), Aha-Val-Asp-Val-Ala-Asp-[CH$_2$—S—S—CH$_2$—CH$_2$—CH$_3$] (SEQ ID No. 64), Aha-Val-Asp-Val-Ala-Asp[CH$_2$—S—S—CH$_2$-Asp-Ala-Val-Asp-Val-Aha] (SEQ ID No. 65), Biotinyl-Aha-Val-Asp-Val-Ala-Asp-[CH$_2$—S—S—CH$_2$—Ph] (SEQ ID NO. 66), Biotinyl-Aha-Val-Asp-Val-Ala-Asp-[CH$_2$—S—S-2-Py] (SEQ ID NO. 67), Biotinyl-Aha-Val-Asp-Val-Ala-Asp-[CH$_2$—S—S—CH$_2$—CH$_2$—CH$_3$] (SEQ ID NO. 68) and Biotinyl-Aha-Val-Asp-Val-Ala-Asp-[CH$_2$—S—S—CH$_2$-Asp-Ala-Val-Asp-Val-Aha] (SEQ ID NO. 69), wherein a is an integer from 0 to 5 and b is an integer from 1 to 7.

7. The compound of claim 6, which is Ac-Val-Asp-Val-Ala-Asp[CHO] (SEQ ID NO. 70).

8. An Ich-1 substrate compound of Formula I:

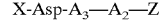

X-Asp-$A_3$—$A_2$—Z     I wherein:
X is $R_1$—(W)$_n$—$A_5$, wherein
$A_5$ is Val;
W is any α-amino acid;
n is an integer of from 0 to 5;
$R_1$ is hydrogen or $R_6$;
$R_6$ is an N-terminal acyl group selected from the group consisting of Aha-, Biotinyl-, Biotinyl-Aha-, $R_3$CO—, $R_3$CH$_2$CO—, $R_3$NHCO—, (R$_4$)$_2$NCO—, and $R_3$OCO— wherein
$R_3$ is selected from the group consisting of t-butyl, i-butyl, n-butyl, n-propyl, i-propyl, c-propyl, ethyl, methyl, c-hexyl, c-hexyl-CH$_2$—, c-hexyl-(CH$_2$)$_2$—, phenyl, phenyl-CH$_2$—, phenyl-(CH$_2$)$_2$—, 4-hydroxyphenyl, 4-hydroxyphenyl-CH$_2$—, and 4-hydroxyphenyl-(CH$_2$)$_2$—; and
$R_4$ is methyl or ethyl;
Asp is aspartic acid;
$A_3$ is an α-amino acid selected from the group consisting of Val, Glu, Thr, Ser, Gln, Ile, Abu, (2-n-Pr)Gly, (2-c-Pr)Gly, (2-t-Bu)Gly and (2-Et)Gly;
$A_2$ is an α-amino acid selected from the group consisting of Ala, Ser, Lys, Val, Met, Gln, Leu, Ile, Abu, His, Orn, Gly, (2-n-Pr)Gly, (2-c-Pr)Gly, (2-t-Bu)Gly and (2-Et)Gly; and
Z is Asp-Y wherein
Asp is aspartic acid; and
Y is selected from the group consisting of 7 amino-4-methylcoumarin, para-nitroaniline, ortho-nitroaniline, and —(Q)$_m$—[CONHR$_2$] wherein
Q is selected from the group consisting of Ala, (2-allyl)Gly, (2-Pr)Gly, Gly, Tyr, and radiolabeled derivatives thereof;

m is 1 or 2;

$R_2$ is H, n-propyl, $CH_2CH_2$(4-hydroxyphenyl), $CH_2$(4-hydroxy-3-methylphenyl), and radiolabeled derivatives thereof.

9. The compound of claim 8, wherein $A_3$ is Val.

10. The compound of claim 8, wherein $A_2$ is Ala.

11. An Ich-1 substrate compound of Formula I:

$$X\text{-Asp-}A_3\text{—}A_2\text{—Z} \qquad I$$

wherein:

X is $R_1$—$A_5$, wherein
$A_5$ is Val;
$R_1$ is selected from the group consisting of $CH_3CO$—, $PhCH_2OCO$—, Aha-, Biotinyl-, and Biotinyl-Aha-;

$A_3$ is Val;

$A_2$ is Ala; and

Z is Asp-Y wherein
Asp is aspartic acid; and
Y is selected from the group consisting of 7-amino-4-methylcoumarin, para-nitroaniline, ortho-nitroaniline, and —(Q)$_m$—[CONHR$_2$] wherein
Q is selected from the group consisting of Ala, (2-allyl)Gly, (2-Pr)Gly, Gly, Tyr, and radiolabeled derivatives thereof,
m is 1 or 2
$R_2$ is H, n-propyl, $CH_2CH_2$(4-hydroxyphenyl), $CH_2$(4-hydroxy-3-methylphenyl), and radiolabeled derivatives thereof.

12. An Ich-1 substrate compound selected from the group consisting of Ac-Val-Asp-Val-Ala-Asp-AMC (SEQ ID NO. 71), Ac-Val-Asp-Val-Ala-Asp-para-NA (SEQ ID NO. 72), Ac-Val-Asp-Val-Ala-Asp-ortho-NA (SEQ ID NO. 73), Ac-Val-Asp-Val-Ala-Asp-[CONHCH$_3$] (SEQ ID NO. 74), Ac-Val-Asp-Val-Ala-Asp-(Q)$_m$—[CONH$_2$] (SEQ ID NO. 75), Ac-Val-Asp-Val-Ala-Asp-Gly-Trp-[CONH$_2$] (SEQ ID NO. 76), Ac-Val-Asp-Val-Ala-Asp-Gly-AMC(SEQ ID NO. 77), Ac-Val-Asp-Val-Ala-Asp-Gly-(2-C($^3$H)H$_2$—C($^3$H)H—CH$_2$)Gly-[CONH$_2$] (SEQ ID NO. 78), Ac-Val-Asp-Val-Ala-Asp-Gly-($^{125}$I)Tyr-[CONH$_2$] (SEQ ID NO. 79), Ac-Val-Asp-Val-Ala-Asp-Gly-(di$^{125}$I)Tyr-[CONH$_2$] (SEQ ID NO. 80), Ac-Val-Asp-Val-Ala-Asp-Gly-[CONHCH$_2$(4-HO-3-$^{125}$I-5Me—Ph)] (SEQ ID NO. 81), Ac-Val-Asp-Val-Ala-Asp-Gly-[CONH(CH$_2$)$_2$(4-HO-3-$^{125}$I—Ph)] (SEQ ID NO. 82), Ac-Val-Asp-Val-Ala-Asp-Gly-[CONH(CH$_2$)$_2$(4-HO-3,5-di$^{125}$I—Ph)] (SEQ ID NO. 83), Biotinyl-Aha-Val-Asp-Val-Ala-Asp-Gly-(2C-($^3$H)H$_2$—C($^3$H)H—CH$_2$)Gly-[CONH$_2$] (SEQ ID NO. 84), Biotinyl-Aha-Val-Asp-Val-Ala-Asp-Gly-($^{125}$I)Tyr-[CONH$_2$] (SEQ ID NO. 85), Biotinyl-Aha-Val-Asp-Val-Ala-Asp-Gly-(di$^{125}$I)Tyr-[CONH$_2$] (SEQ ID NO. 86), Biotinyl-Aha-Val-Asp-Val-Ala-Asp-Gly[CONHCH$_2$(4-HO-3-$^{125}$I-5-Me—Ph)] (SEQ ID NO. 87), Biotinyl-Aha-Val-Asp-Val-Ala-Asp-Gly-[CONH(CH$_2$)$_2$(4-HO-3-$^{125}$I—Ph)] (SEQ ID NO. 88), and Biotinyl-Aha-Val-Asp-Val-Ala-Asp-Gly-[CONH(CH$_2$)$_2$(4-HO-3,5-di$^{125}$I—Ph)] (SEQ ID NO. 89), wherein Q is selected from the group consisting of Ala, (2-allyl)Gly, (2-Pr)Gly, Tyr, and radiolabeled derivatives thereof; and m is 1 or 2.

13. The compound of claim 12, which is Ac-Val-Asp-Val-Ala-Asp-AMC (SEQ ID NO. 71).

14. The compound of claim 12, which is Ac-Val-Asp-Val-Ala-Asp-para-NA (SEQ ID NO. 72).

15. The compound of claim 12, which is Ac-Val-Asp-Val-Ala-Asp-ortho-NA (SEQ ID NO. 73).

16. A method for inhibiting the proteolytic activity of Ich-1 comprising contacting Ich-1 with a compound of claims 5, 6 or Formula I:

$$X\text{-Asp-}A_3\text{—}A_2\text{—Z} \qquad I$$

wherein:

X is $R_1$—(W)$_n$—$A_5$, wherein
$A_5$ is selected from the group consisting of Val, Ile, Tyr, Phe, Leu, Thr, Asn, Cha, Abu, (2-n-Pr)Gly, (2-c-Pr)Gly, (2-t-Bu)Gly and (2-Et)Gly;
W is any α-amino acid;
n is an integer from 0 to 5;
$R_1$ is hydrogen or $R_6$;
$R_6$ is an N-terminal acyl group selected from the group consisting of Aha-, Biotinyl-, Biotinyl-Aha-, $R_3CO$—, $R_3CH_2CO$—, $R_3NHCO$—, $(R_4)_2NCO$—, and $R_3OCO$— wherein
$R_3$ is selected from the group consisting of t-butyl, i-butyl, n-butyl, n-propyl, i-propyl, c-propyl, ethyl, methyl, c-hexyl, c-hexyl-$CH_2$—, c-hexyl-$(CH_2)_2$—, phenyl, phenyl-$CH_2$—, phenyl-$(CH_2)_2$—, 4-hydroxyphenyl, 4-hydroxyphenyl-$CH_2$—, and 4-hydroxyphenyl-$(CH_2)_2$—; and
$R_4$ is methyl or ethyl;

Asp is aspartic acid;

$A_3$ is an α-amino acid selected from the group consisting of Val, Glu, Thr, Ser, Gin, Ile, Abu, (2-n-Pr)Gly, (2-c-Pr)Gly, (2-t-Bu)Gly and (2-Et)Gly;

$A_2$ is an α-amino acid selected from the group consisting of Ala, Ser, Lys, Val, Met, Gln, Leu, Ile, Abu, His, Om, Gly, (2-n-Pr)Gly, (2-c-Pr)Gly, (2-t-Bu)Gly and (2-Et)Gly; and Z is $A_1$, wherein:
$A_1$ is a C-terminally-modified residue selected from the group consisting of Asp[CHO], Asp[CN], Asp[COCHN$_2$], Asp [COCH$_2$Cl], Asp[COCH$_2$Br], Asp[COCH$_2$F], Asp[COCH$_2$OCO-Aryl], Asp[COCH$_2$OCO-Heteroaryl], Asp[COCH$_2$O(CH$_2$)$_a$-Aryl], Asp[COCH$_2$O(CH$_2$)$_a$-Heteroaryl], Asp[COCH$_2$S(CH$_2$)$_a$-Aryl], Asp[COCH$_2$S(CH$_2$)$_a$-Heteroaryl], Asp[CO(CH$_2$)$_b$-Aryl], Asp[CO(CH$_2$)$_b$-Heteroaryl], Asp[CH$_2$S—R$_5$], Glu[CHO], Glu[CN], Glu[COCHN$_2$], Glu[COCH$_2$Cl], Glu[COCH$_2$Br], Glu[COCH$_2$F], Glu[COCH$_2$OCO-Aryl], Glu[COCH$_2$OCO-Heteroaryl], Glu[COCH$_2$O(CH$_2$)$_a$-Aryl], Glu[COCH$_2$O(CH$_2$)$_a$-Heteroaryl], Glu[COCH$_2$S(CH$_2$)$_a$-Aryl], Glu[COCH$_2$S(CH$_2$)$_a$-Heteroaryl], Glu[CO(CH$_2$)$_b$-Aryl], Glu[CO(CH$_2$)$_b$-Heteroaryl], and Glu[CH$_2$SR$_5$] wherein
a is an integer from 0 to 5;
b is an integer from 1 to 7; and
$R_5$ is selected from the group consisting of —S-alkyl, —S-cycloalkyl, —S-(cycloalkyl)alkyl, —S-aryl, —S-arylalkyl, —S-heterocycle, —S-(heterocycle)alkyl, —S-heteroaryl, —S-heteroarylalkyl, X-Asp-A$_3$—A$_2$-Asp(CH$_2$S)—, and X-Asp-A$_3$—A$_2$-Glu(CH$_2$S)— such that the proteolytic activity of Ich-1 is inhibited.

17. The method of claim 16, wherein Ich-1 is within an isolated preparation.

18. The method of claim 16, wherein Ich-1 is within a cell.

19. A method for detecting the presence of Ich-1 in a sample, comprising contacting a sample with the compound of claims 11, 12 or Formula I:

$$X\text{-Asp-}A_3\text{—}A_2\text{—Z} \qquad I$$

wherein:

X is $R_1$—(W)$_n$—$A_5$, wherein
$A_5$ is a α-amino acid selected from the group consisting of Val, Ile, Tyr, Phe, Leu, Thr, Asn, Cha, Abu, (2-n-Pr)Gly, (2-c-Pr)Gly, (2-t-Bu)Gly and (2-Et)Gly;

W is any α-amino acid;

n is an integer of from 0 to 5;

$R_1$ is hydrogen or $R_6$;

$R_6$ is an N-terminal acyl group selected from the group consisting of Aha-, Biotinyl-, Biotinyl-Aha-, $R_3CO$—, $R_3CH_2CO$—, $R_3NHCO$—, $(R_4)_2NCO$—, and $R_3OCO$— wherein $R_3$ is selected from the group consisting of t-butyl, i-butyl, n-butyl, n-propyl, i-propyl, c-propyl, ethyl, methyl, c-hexyl, c-hexyl-$CH_2$—, c-hexyl-$(CH_2)_2$—, phenyl, phenyl-$CH_2$—, phenyl-$(CH_2)_2$—, 4-hydroxyphenyl, 4-hydroxyphenyl-$CH_2$—, and 4-hydroxyphenyl-$(CH_2)_2$—; and $R_4$ is methyl or ethyl;

Asp is aspartic acid;

$A_3$ is an α-amino acid selected from the group consisting of Val, Glu, Thr, Ser, Gln, Ile, Abu, (2-n-Pr)Gly, (2-c-Pr)Gly, (2-t-Bu)Gly and (2-Et)Gly;

$A_2$ is an α-amino acid selected from the group consisting of Ala, Ser, Lys, Val, Met, Gln, Leu, Ile, Abu, His, Orn, Gly, (2-n-Pr)Gly, (2-c-Pr)Gly, (2-t-Bu)Gly and (2-Et)Gly; and Z is Asp-Y wherein Asp is aspartic acid; and Y is selected from the group consisting of 7 amino-4-methylcoumarin, para-nitroaniline, ortho-nitroaniline, and —$(Q)_m$—[$CONHR_2$] wherein Q is selected from the group consisting of Ala, (2-allyl)Gly, (2Pr)Gly, Gly, Tyr, and radiolabeled derivatives thereof;

m is 1 or 2;

$R_2$ is H, n-propyl, $CH_2CH_2$(4-hydroxyphenyl), $CH_2$(4-hydroxy-3-methylphenyl), and radiolabeled derivatives thereof, and measuring the amount of proteolytic cleavage of the compound, wherein proteolytic cleavage of the compound is indicative of the presence of Ich-1 in the sample.

20. A method for isolating Ich-1 from a mixture of substances, comprising contacting a mixture of substances with the compound of claims 5, 6, or Formula I:

$$X\text{-Asp-}A_3\text{—}A_2\text{—}Z \quad\quad I$$

wherein:

X is $R_1$—$(W)_n$—$A_5$, wherein $A_5$ is selected from the group consisting of Val, Ile, Tyr, Phe, Leu, Thr, Asn, Cha, Abu, (2-n-Pr)Gly, (2-c-Pr)Gly, (2-t-Bu)Gly and (2-Et)Gly;

W is any α-amino acid;

n is an integer from 0 to 5;

$R_1$ is hydrogen or $R_6$;

$R_6$ is an N-terminal acyl group selected from the group consisting of Aha-, Biotinyl-, Biotinyl-Aha-, $R_3CO$—, $R_3CH_2CO$—, $R_3NHCO$—, $(R_4)_2NCO$—, and $R_3OCO$— wherein $R_3$ is selected from the group consisting of t-butyl, i-butyl, n-butyl, n-propyl, i-propyl, c-propyl, ethyl, methyl, c-hexyl, c-hexyl-$CH_2$—, c-hexyl-$(CH_2)_2$—, phenyl, phenyl-$CH_2$—, phenyl-$(CH_2)_2$—, 4-hydroxyphenyl, 4-hydroxyphenyl-$CH_2$—, and 4-hydroxyphenyl-$(CH_2)_2$—; and $R_4$ is methyl or ethyl;

Asp is aspartic acid;

$A_3$ is an α-amino acid selected from the group consisting of Val, Glu, Thr, Ser, Gln, Ile, Abu, (2-n-Pr)Gly, (2-c-Pr)Gly, (2-t-Bu)Gly and (2-Et)Gly;

$A_2$ is an α-amino acid selected from the group consisting of Ala, Ser, Lys, Val, Met, Gln, Leu, Ile, Abu, His, Orn, Gly, (2-n-Pr)Gly, (2-c-Pr)Gly, (2-t-Bu)Gly and (2-Et)Gly; and Z is $A_1$, wherein:

$A_1$ is a C-terminally-modified residue selected from the group consisting of Asp[CHO], Asp[CN], Asp[$COCHN_2$], Asp[$COCH_2Cl$], Asp[$COCH_2Br$], Asp[$COCH_2F$], Asp[$COCH_2OCO$-Aryl], Asp[$COCH_2OCO$-Heteroaryl], Asp[$COCH_2O(CH_2)_a$-Aryl], Asp[$COCH_2O(CH_2)_a$-Heteroaryl], Asp[$COCH_2S(CH_2)_a$-Aryl], Asp[$COCH_2S(CH_2)_a$-Heteroaryl], Asp[$CO(CH_2)_b$-Aryl], Asp[$CO(CH_2)_b$-Heteroaryl], Asp[$CH_2S$—$R_5$], Glu[CHO], Glu[CN], Glu[$COCHN_2$], Glu[$COCH_2Cl$], Glu[$COCH_2Br$], Glu[$COCH_2F$], Glu[$COCH_2OCO$-Aryl], Glu[$COCH_2OCO$-Heteroaryl], Glu[$COCH_2O(CH_2)_a$-Aryl], Glu[$COCH_2O(CH_2)_a$-Heteroaryl], Glu[$COCH_2S(CH_2)_a$-Aryl], Glu[$COCH_2S(CH_2)_a$-Heteroaryl], Glu[$CO(CH_2)_b$-Aryl], Glu[$CO(CH_2)_b$-Heteroaryl], and Glu[$CH_2SR_5$] wherein a is an integer from 0 to 5;

b is an integer from 1 to 7; and $R_5$ is selected from the group consisting of —S-alkyl, —S-cycloalkyl, —S-(cycloalkyl)alkyl, —S-aryl, —S-arylalkyl, —S-heterocycle, —S-(heterocycle)alkyl, —S-heteroaryl, —S-heteroarylalkyl, X-Asp-$A_3$—$A_2$—Asp($CH_2S$)—, and X-Asp-$A_3$—$A_2$-Glu($CH_2S$)—;

wherein the compound is immobilized, such that Ich-1 within the mixture of substances binds to the compound, thereby forming immobilized Ich-1; separating immobilized Ich-1 from the mixture of substances; disrupting the interaction between immobilized Ich-1 and the compound; and recovering Ich-1 such that Ich-1 is isolated from the mixture of substances.

21. A pharmaceutical composition comprising the compound of any of claims 1, 5, 6, 8, 11, or 12 and a pharmaceutically acceptable carrier.

* * * * *